United States Patent
McCreery et al.

(10) Patent No.: US 12,302,860 B2
(45) Date of Patent: May 20, 2025

(54) HEARING PROTECTION DEVICES AND METHODS FOR ANIMALS

(71) Applicant: Zeteo Tech, Inc., Sykesville, MD (US)

(72) Inventors: Thomas McCreery, Sykesville, MD (US); Michael McLoughlin, Sykesville, MD (US); Evelyn McCreery, Tucson, AZ (US); Noella A. Bryden, Sykesville, MD (US); Stuart Collymore, Sykesville, MD (US); Thomas Sager, Whispering Pines, NC (US); Rebecca Baxter, Spring Lake, NC (US)

(73) Assignee: Zeteo Tech, Inc., Sykesville, MD (US)

( * ) Notice: Subject to any disclaimer, the term of this patent is extended or adjusted under 35 U.S.C. 154(b) by 701 days.

(21) Appl. No.: 17/275,179

(22) PCT Filed: Sep. 15, 2019

(86) PCT No.: PCT/US2019/051206
§ 371 (c)(1),
(2) Date: Mar. 10, 2021

(87) PCT Pub. No.: WO2020/091899
PCT Pub. Date: May 7, 2020

(65) Prior Publication Data
US 2022/0039353 A1    Feb. 10, 2022

Related U.S. Application Data

(60) Provisional application No. 62/900,460, filed on Sep. 14, 2019, provisional application No. 62/731,866, filed on Sep. 15, 2018.

(51) Int. Cl.
*A01K 13/00* (2006.01)
*H04W 4/80* (2018.01)

(52) U.S. Cl.
CPC .............. *A01K 13/006* (2013.01); *H04W 4/80* (2018.02)

(58) Field of Classification Search
CPC ........ A01K 13/006; H04W 4/80; A61F 11/14; A61F 11/145
(Continued)

(56) References Cited

U.S. PATENT DOCUMENTS 2,710,972 A * 6/1955 Radnofsky ............... A42B 3/10
2/410
3,870,544 A * 3/1975 Shisko ..................... B05D 7/06
162/181.2
(Continued)

FOREIGN PATENT DOCUMENTS

DE    202007003939    7/2007
JP    2009505786 A    2/2009
(Continued)

OTHER PUBLICATIONS

Written Opinion of the ISA/KIPO mailed on Jul. 6, 2020 for PCT/US2019/051206.

*Primary Examiner* — Timothy D Collins
*Assistant Examiner* — Maria E Graber
(74) *Attorney, Agent, or Firm* — Paradice & Li LLP; Anand S. Chellappa

(57) ABSTRACT

Passive noise reduction components provide reduction of at least 20 dB to 30 dB in dogs using flexible soft muffs that are housed in a hearing protection sleeve. Active noise cancellation (ANC) features may also be used to increase noise reduction to about 40 dB over a large frequency range. The devices may employ passive noise reduction electronic bypass to measure and playback sounds at safe levels bypassing at least one of ANC and passive noise reduction. Communication components may be employed for communication between the handler and the animal. The systems
(Continued)

and methods may be used to protect the hearing and utility of military working dogs and hunting dogs.

24 Claims, 12 Drawing Sheets

(58) Field of Classification Search
USPC .............................. 119/850, 856; 2/171, 410
See application file for complete search history.

(56) References Cited

U.S. PATENT DOCUMENTS

| | | | | |
|---|---|---|---|---|
| 4,452,841 A * | 6/1984 | Oliveira | ............... | G10K 11/165 |
| | | | | 181/294 |
| 4,985,925 A * | 1/1991 | Langberg | ......... | G10K 11/17861 |
| | | | | 381/71.13 |
| 5,003,631 A * | 4/1991 | Richardson | .............. | A42B 3/30 |
| | | | | 2/6.1 |
| 5,010,773 A * | 4/1991 | Lorenz | ..................... | G01L 25/00 |
| | | | | 73/862.041 |
| 5,500,958 A * | 3/1996 | Falco | ....................... | A61F 11/14 |
| | | | | 2/209 |
| 5,622,662 A * | 4/1997 | Veiga | ..................... | F16F 9/306 |
| | | | | 156/247 |
| 5,893,173 A * | 4/1999 | Bray | .................... | A01K 13/006 |
| | | | | 119/850 |
| 6,278,786 B1 | 8/2001 | McIntosh | | |
| 6,467,096 B1 * | 10/2002 | Coluccio | .................. | A42B 1/22 |
| | | | | 2/195.2 |
| 6,837,191 B2 * | 1/2005 | Brewington | ........... | A01K 23/00 |
| | | | | 119/869 |
| 7,058,368 B2 | 6/2006 | Nicholls | | |
| 7,743,736 B2 | 6/2010 | Winestock | | |
| 8,015,948 B2 * | 9/2011 | Hall | ..................... | A01K 13/006 |
| | | | | 54/79.1 |
| 8,161,668 B2 * | 4/2012 | Ketzenberg | .............. | A61D 9/00 |
| | | | | 36/7.1 R |
| 8,227,520 B2 * | 7/2012 | Shirasaki | ................... | C08J 9/28 |
| | | | | 524/588 |
| 8,534,290 B2 * | 9/2013 | Karrman | .................. | A61F 11/14 |
| | | | | 128/867 |
| 9,051,445 B2 * | 6/2015 | Nozoe | ..................... | C08G 77/12 |
| 9,107,011 B2 * | 8/2015 | Broadley | ......... | G10K 11/17885 |
| 9,585,792 B2 * | 3/2017 | Fairclough | ........... | A42B 1/0188 |
| 9,591,879 B2 * | 3/2017 | Michlitsch | ............. | A41D 13/05 |
| 9,628,895 B2 | 4/2017 | Malaviya | | |
| 9,654,854 B2 | 5/2017 | Darlington | | |
| 10,149,786 B1 * | 12/2018 | Halfaker | .......... | G10K 11/17881 |
| 2002/0141599 A1 | 10/2002 | Trajkovic | | |
| 2007/0062462 A1 * | 3/2007 | McGuire | ............... | A01K 13/006 |
| | | | | 119/850 |
| 2008/0282448 A1 * | 11/2008 | Cho | ......................... | A42C 5/02 |
| | | | | 2/181 |
| 2009/0178177 A1 * | 7/2009 | Fairclough | ........... | A42B 1/0188 |
| | | | | 2/209 |
| 2009/0178628 A1 * | 7/2009 | Carmean | .............. | A01K 27/002 |
| | | | | 119/850 |
| 2009/0314298 A1 * | 12/2009 | Hansson | ................. | A61F 11/14 |
| | | | | 2/209 |
| 2010/0119076 A1 | 5/2010 | Monk | | |
| 2011/0225705 A1 | 9/2011 | Fernandes et al. | | |
| 2011/0297107 A1 * | 12/2011 | Kostelec | ............ | A01K 13/006 |
| | | | | 119/850 |
| 2012/0014532 A1 | 1/2012 | Kimura | | |
| 2015/0294662 A1 | 10/2015 | Ibrahim | | |
| 2015/0342716 A1 * | 12/2015 | Haught | ................ | A01K 13/006 |
| | | | | 119/855 |
| 2016/0193084 A1 | 7/2016 | Jenkins | | |
| 2018/0014597 A1 * | 1/2018 | Cooke | .................... | A42B 3/042 |
| 2019/0141951 A1 * | 5/2019 | Coughlan | ............ | A01K 13/006 |
| | | | | 119/850 |

FOREIGN PATENT DOCUMENTS

| | | |
|---|---|---|
| JP | 003164772 U | 12/2010 |
| JP | 003201076 U | 11/2015 |
| JP | 2014068831 A | 4/2024 |
| KR | 1020020029826 | 4/2002 |
| KR | 101202708 B1 | 11/2012 |
| WO | 1997048296 A1 | 12/1997 |
| WO | 2018137037 | 8/2018 |
| WO | 2020033032 | 2/2020 |

* cited by examiner

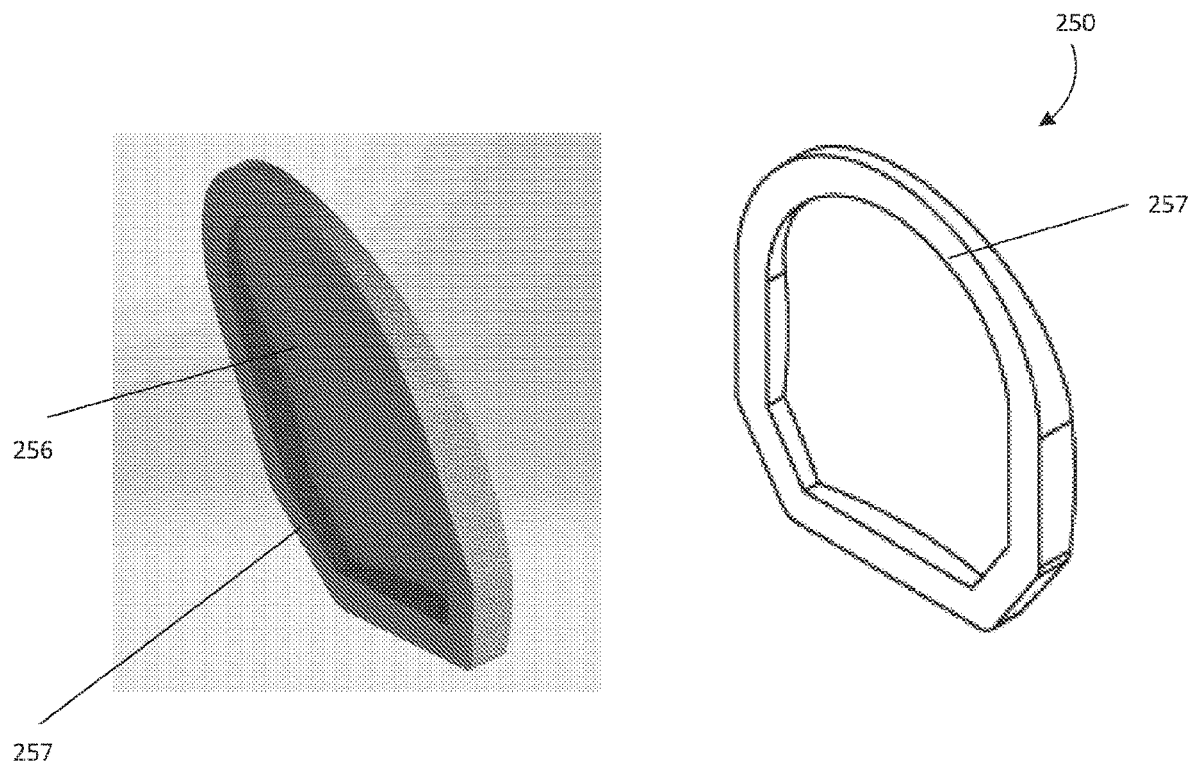
FIG. 13A.
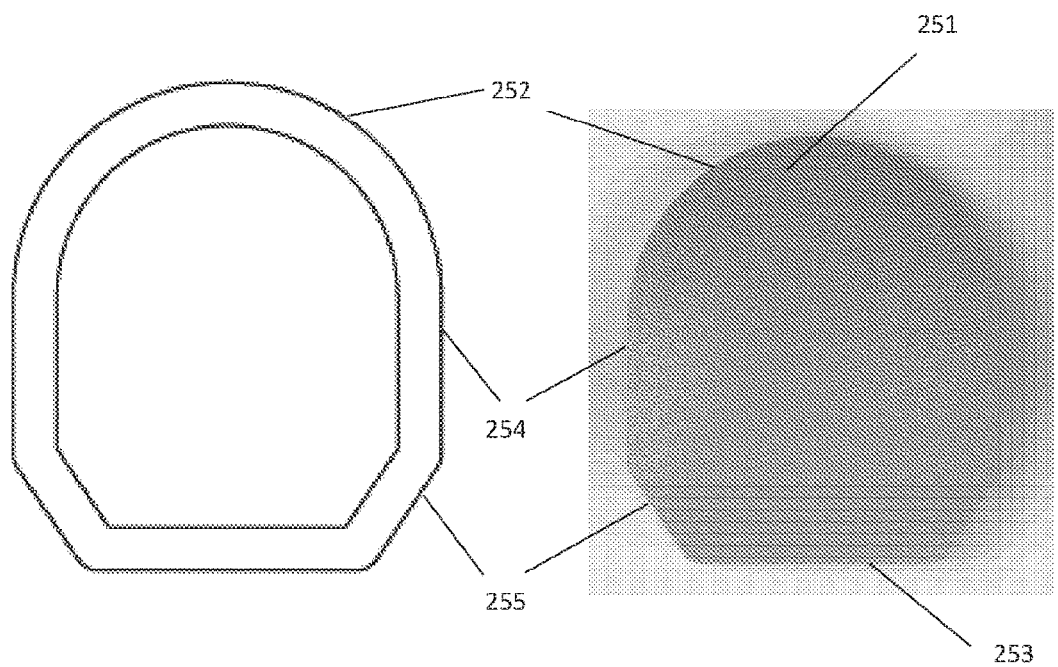
FIG. 13B.
FIG. 13C.

HEARING PROTECTION DEVICES AND METHODS FOR ANIMALS

RELATED APPLICATIONS

This application is a U.S. National Stage Application of International Application No. PCT/US2019/051206, filed Sep. 15, 2019, which is related to and claims the benefit of U.S. Provisional Application No. 62/731,866, filed Sep. 15, 2018, and titled "Hearing Protection Devices and Methods for Animals," and U.S. Provisional Application No. 62/900,460, filed Sep. 14, 2019, and titled "Hearing Protection Devices and Methods for Animals," the entire disclosures of which are incorporated herein by reference in their entireties.

GOVERNMENT RIGHTS

This invention was made under contract with the United States Army Research Office, under Contract No. W911NF-18-C-0016, and the United States Government may have certain rights in the invention.

FIELD

The present invention relates to systems and methods for enhanced hearing protection for dogs and other animals. In particular, the systems and methods mitigate hearing loss in animals such as military working dogs and hunting dogs using passive and active noise reduction.

BACKGROUND

Military working dogs (MWDs) are vulnerable to suffer from severe hearing impairment (SHI) due to the auditory assault caused during combat and non-combat training. MWD training has been reported to cost $80,000 to $100,000 per dog. Noise Induced Hearing Loss (NIHL) has also been reported as an issue for hunting dogs and MWDs. As in humans, the main mechanism of NIHL is hair cell damage, but extreme noise can also rupture the tympanic membrane or cause damage to the ossicles. In addition, the noise level in kennels can cause cumulative damage. Despite well documented evidence that noise in a military environment can damage a working dog's hearing and degrade its performance, limited options are available for hearing protection. While over-ear solutions (e.g. Mutt Muffs) provide some level of protection for high noise environments (e.g. aircraft, auto racing, concerts), their effectiveness and utility in a military or active environment is limited. Military working dogs and hunting dogs may spend significant time in high noise environments, exposing them to significantly higher instantaneous and average noise levels, which can result in acute and chronic hearing degradation.

Noise affecting MWD in military environment is caused by a variety of sources that includes impact or impulse noise from weapons or explosive devices, broadband noise from machinery such as turbines and jet engines, tonal noise from rotating machinery such as helicopter blades and internal combustion engines, vocalization by humans (including but not limited to speech), and kennel noise. These sources contribute to overall noise levels, lead to hearing loss and create challenges for the handler. FIG. 1 displays sound levels (dBA) for broadband sources and impulse sources (dBP) for some noises present in military operations. The measured noise levels in the cockpit of Army helicopters is reported to be at least 106 dBA, and sound levels of at least 122 dB SPL (sound pressure level) in an operating military helicopter has been reported. Helicopters generate lower frequency sound spectra (below ~1000 Hz), typically dominated by tonal components. The effects of this noise level on hearing in a short 30-minute helicopter flight is illustrated in FIG. 2. As shown, a Temporary Threshold Shift (TTS) of approximately 50 dB SPL is induced by exposure to noise. It is likely that upon exiting the aircraft or a high noise environment, normal vocal commands will not be heard or will be misinterpreted by the dog at a critical juncture.

Despite well documented evidence that noise in domestic and military environments can damage a dog's hearing and degrade their performance, limited options for hearing protection exist. Dogs kept as pets are also exposed to high noise levels in a wide range of environments (e.g., kennels, grooming, aircraft, auto racing, concerts, hunting, and fireworks). Of the approximately 90 million dogs living as pets in the United States, it is estimated that up to one third experience anxiety due to environmental noise, especially during holidays such as the Fourth of July.

U.S. Pat. No. 9,628,895 entitled "Animal Headphone Apparatus," describes a modified headphone device specifically suited for use with dogs so that an owner may allow their dog or other pet to listen to music. The owner may also use the headphones to command, train or monitor their pet. A first earpiece and a second earpiece are oriented inward and downward to account for the substantially vertical structure of a canine ear canal. A chipset and a power source provide capability for several features, including an integrated music player, at least one camera, a microphone, a vibration producing device, a global positioning system device, and at least one digital display for video viewing by the dog or other pet. A wireless communication device allows a user to control various features through a smart phone or remote control. This device is a headset which allows the owner to play music or speak to the dog and is intended to help soothe and calm the dog without requiring the owner to listen to the same music. The system is not intended to protect the dog's hearing from loud noises.

International Pat. Pub. No. WO2009134863 entitled "Method and Apparatus for Protective Head Gear For Use in Animals" describes an animal headband and a method of use of the animal headband as a protective head gear for animals. The head gear provides a substantially uniform compression force against the entire circumference of the head of the animal to securely position the ear flaps of the animal over the ear canal. The protective head gear further secures the ear flaps of the animal away from the ear canal, so as to facilitate medical procedures and subsequent healing from medical procedures involving the ear canal. The headband may be made of materials such as cotton, spandex, polyester, nylon, rayon, line. This patent application focuses on positioning the ear flaps to provide hearing protection with the pinna of the ear folded over the opening of the ear canal and does not disclose any noise reduction realized beyond that offered by the headband material itself and the folded ear flap in grooming and medical office settings.

Commercially available Mutt Muffs (sold by Safe and Sound Pets LLC, Westminster, MD) are an adaptation of ear muffs similar to those designed for humans with straps to hold the muff in place. These over-the-ear muffs utilize a hard-backed shell lined with an acoustic foam. A soft foam ring is joined to the edges along the circumference of the acoustic foam to create a seal around the ear. Any break in the seal will significantly degrade noise reduction. Mutt Muffs utilize a set of straps to hold the muffs in place in each ear. A major deficiency of the Mutt Muff is the inability to maintain a good seal between the hardbacked shell and the dogs head. Commercially available Happy Hoodie is designed to reduce anxiety and provide comfort to the dog by applying pressure to simulate a sense of envelopment. The Happy Hoodie, designed specifically for wrapping the head, does claim some level of noise reduction. However, the Happy Hoodie does not employ any means of reducing noise beyond that offered by the fabric of the wrap.

Hearing protection devices (HPD) are traditionally divided into two categories, namely, linear devices in which sound attenuation is constant and does not depend on the external sound level, and non-linear devices in which attenuation is a function of the amplitude and frequency of the environmental sound level. Non-linear devices are generally of two varieties, namely, (1) passive sound attenuation devices such as earplugs and ear muffs that incorporate a mechanical filter mechanism to provide protection against loud, impulse noise while allowing low level sounds to pass, and (2) passive attenuation combined with electronic noise reduction such as active noise cancellation (ANC) systems in which sound is measured with a reference microphone and filtered to generate a canceling noise signal. Non-linear devices can also protect the ear against loud, impulsive noise by changing the gain as a function of the overall noise level. Purely passive approaches typically utilize a mechanical device such as a tuned filter with variable acoustic impedance; for example, it may comprise a cylindrical cavity perforated at either end, which is inserted into an earplug. In low noise environments, sounds are transmitted easily through the cavity, while in high noise environments the impedance of the cavity increases, attenuating loud sounds. Electronic approaches combine passive noise reduction (with or without ANC) with noise reduction bypass capabilities. Electronic bypass approaches combine passive noise reduction with an external microphone or other means to sense environmental sounds that are then compressed or filtered for play back at an appropriately reduced level via a miniature acoustic source (speaker) placed inside the HPD close to the listener's ear. In low noise environments, sound electronically bypasses passive noise reduction, and amplification can provide an almost unaltered perception of faint or moderate level sounds such as oral communication. In higher noise environments, the gain is reduced to prevent potentially hazardous noises from being electronically transmitted. That is, in quiet environments, sounds may be amplified, and in loud environments playback may be reduced with bypass eventually turned off at high noise levels. Passive noise reduction bypass works over frequency ranges of about 100 Hz to about 15 kHz. A means to detect impulse noise that may saturate the system may also be incorporated to provide a means to mute the input and prevent the system from becoming unstable or acting in an unpredictable or undesirable way. The same components such as, external and internal microphones, and speaker may be used for non-linear hearing protection devices incorporating bypass of passive noise reduction and ANC systems. In ANC systems, the canceling signal is typically generated using a small speaker or acoustic receiver. ANC systems work best at lower frequencies (<1000 Hz) and are most effective when combined with passive attenuation. Internal microphones may also be used to measure the level of attenuation in situ and provide feedback related to the effective use or installation of the device on the dog's head that may alert the dog's handler to re-position the hearing protection device.

Broadband noise can be produced by a variety of sources including impulsive sources (e.g. gunshot or explosive) or machinery. Both have significant noise components with frequency in the range of 10 Hz to 10 kHz and can produce components at higher frequencies that are beyond the range of human hearing (e.g. noise from a rifle). On the other hand, aircraft with rotating blades (helicopters, turbo props) frequently generate lower frequency spectra, typically dominated by tonal components. Passive earplugs are very effective in reducing noise above 500 Hz but are less effect at lower frequencies (FIG. 3), thereby limiting the effectiveness of the passive system. Addition of Active Noise Control (ANC) can significantly improve performance (FIG. 4) at low frequencies but produce minimal additional attenuation above 500 Hz.

Hearing protection devices and methods for dogs should be able to meet several unique challenges. First, the shape and size of the external ear of dogs (pinna) vary according to the size and breed of the dog. This variability is much greater than that for humans, making it ineffective to directly translate systems designed for human hearing protection to a canine. This variation not only includes the size and shape of the head, but also the size of the pinna relative to the head. The hearing protection device must be configurable to cover these variations to completely and effectively enclose the ear canal preferably without folding the pinna over the ear canal. Second, there is much greater variability in the shape of the canine head from breed-to-breed compared to the human head. Finally, maintaining a good fit in an active canine (e.g., military working dogs, hunting dogs) provides additional challenges related to keeping the device held in place even when the dog is running through bushes and the like. Robust devices and methods for protecting against hearing loss for a wide range of dog breeds and sizes are required.

BRIEF DISCLOSURE

Disclosed is an exemplary hearing protection device for a dog comprising a sleeve made of stretchable fabric configured to slip on/off the dog's head and having an inside surface, a pair of passive noise reduction components, one for each ear, disposed on the inside surface of the sleeve and configured to form a seal with the surface of each external ear of the dog when the sleeve is installed on the dog's head, and a drawstring for removably tightening the sleeve to the dog's neck to create the seal between each of the noise reduction components and the surface of each of the dog's external ear wherein the inside surface of the sleeve is in contact with the dog's head when the sleeve is installed. The sleeve may be made of a material comprising elastane. The elastane material may comprise nylon and spandex. The elastane material may comprise between about 60% to about 70% nylon and between about 30% and about 40% spandex. The elastane material may comprise between about 65% to about 70% nylon, and the remaining being spandex. The drawstring may be inserted through a plurality of grommets disposed in the sleeve and adjustably tightened to the dog's neck using a stop-cord lock. The hearing protection device may further comprise a reinforcing wear strip disposed substantially along the center line position of the length of the sleeve and joined to an outside surface of the sleeve disposed opposite to the inside surface of the sleeve. For large dogs, the length of the sleeve may be between about 15 in. and about 17 in. and the width of the sleeve may be between about 8 in. and about 10 in. The dimensions of the sleeve may be varied depending on the size of the dog to achieve a good fit with the dog's head. Each passive noise reduction component may comprise a flexible composite structure made of polymeric closed cell foam materials.

Each passive noise reduction component may comprise a first polymeric closed cell foam material having a mass loaded vinyl ("MLV") material backing on one side and a second closed cell foam material ring disposed along the edges of the first foam material on the side opposite to that having the MLV backing. The second closed cell foam material ring may be configured to form a seal between each of the dog's external ear and each of the noise reduction components. Each of the first and second closed cell foam material may comprise at least one of EPDM (ethylene propylene diene monomer), neoprene, and chloroprene rubber comprising polymers with densities ranging between about 5 lb/ft$^3$ and about 7 lb/ft$^3$. The MLV material may comprise barium infused mass loaded polyvinyl chloride. The thickness of the first closed cell foam material having the MLV backing may be between about 0.45 in. and about 0.65 in. The weight to area ratio of the first and second closed cell foam material may be between about 0.2 lb/ft$^2$ and about 0.25 lb/ft$^2$. The thickness of each passive noise reduction component may between about 0.8 in. and about 1.5 in.

An exemplary hearing protection device may further comprise passive noise reduction electronic bypass components wherein the amplitude of sound playback into each of the dog's ears may be adjusted depending upon external sound levels and at external sound frequencies between about 100 Hz and about 15 kHz. The electronic bypass components may comprise external and internal microphones for each ear, a speaker for each ear, and a control module. The internal microphone and speaker for each ear may be substantially housed within the passive noise reduction component corresponding to that ear while the external microphone can be positioned on an outer surface. An exemplary hearing protection device may further comprise active noise cancellation (ANC) components comprising an internal microphone for each ear, an external microphone for each ear, a speaker for each ear, and a control module capable of attenuating external noise at frequencies below about 1000 Hz in each of the dog's ear. The internal microphone and speaker corresponding to each ear may be substantially housed within the passive noise reduction component for that ear. The control module may be mounted on the dog's collar.

In an exemplary hearing protection device, the passive noise reduction component corresponding to each ear may comprise a molded cup made of at least one of a polyurethane foam and liquid silicone rubber wherein the cup is shaped to conform to the shape of dog's head and ears.

Disclosed is an exemplary hearing protection device for a dog comprising a sleeve made of stretchable fabric configured to slip on/off the dog's head having an inside surface, a pair of passive noise reduction components or flexible soft muffs disposed on the internal surface of the sleeve and each configured to form a seal with the surface of each external ear of the dog when the sleeve is installed on the dog's head, a drawstring for removably tightening the sleeve to the dog's neck to create the seal between each of the noise reduction components and the surface of each of the dog's external ear, at least one of passive noise reduction electronic bypass components and ANC components for adjusting the level of noise reduction in each of the dog's ear, and a communication component configured to enable the dog's handler to communicate with the dog. The inside surface of the sleeve is in contact with the dog's head when the sleeve is installed on the dog's head. Each passive noise reduction component may comprise a composite structure made of polymeric closed cell foam materials. The communication component may comprise at least one of a radio, radio receiver, a Bluetooth® communication device, a wireless communication device, an antenna, and a user interface unit. The passive noise reduction electronic bypass components may comprise an external microphone, a speaker and a control module. The internal microphone and speaker for each ear may be substantially housed within the passive noise reduction component for that ear. The ANC components may comprise an internal microphone, an external microphone, a speaker, and a control module capable of attenuating external noise at frequencies below about 1000 Hz in each of the dog's ear. The internal microphone and speaker for each ear may be substantially housed within each of the passive noise reduction components.

Disclosed is an exemplary method for protecting a dog's hearing using any one of the disclosed exemplary devices, the method comprising slipping any one of the disclosed exemplary devices on to the dog's head, aligning each the passive noise reduction component with each of the dog's external ear, and removably tightening the device by adjusting the drawstring to create a seal between the noise reduction component and the corresponding external ear. An exemplary method may further comprise enhancing noise reduction in each of the dog's ear using at least one of passive noise reduction electronic bypass and ANC and transmitting communication from the dog's handler to the dog. The transmitting step may be effected using at least one of radio, Bluetooth®, and wireless devices. The transmitting step may comprise bypassing at least one of ANC and electronic passive noise reduction bypass and transmitting encrypted commands to the dog at frequencies greater than about 20 kHz. The transmitting step may comprise bypassing at least one of ANC and electronic passive noise reduction bypass and transmitting encrypted commands to the dog frequencies between about 20 kHz and about 40 kHz. An exemplary method may further comprise unencrypting handler communication at the dog's ear to the audible frequency range of between about 2 kHz and about 4 kHz.

Disclosed is an exemplary method for fabricating a hearing protection device for a dog, the method comprising collecting customer provided input information transmitted using a software application installed in a customer's mobile communication device comprising at least one of the dog's breed, the dog's age, environmental information to which the dog would be exposed to including but not limited to environmental noise decibels levels and frequency, and at least one of a photograph and video recording showing front and side views of the dog, processing the collected information and determining at least one of the size of the hearing protection device, the structure and size of the noise reduction component, whether at least one of ANC and passive sound reduction bypass is required, and creating a 3D computer model of the dog's head and the device using the collected and processed information and testing the fit of the device, and fabricating the device to substantially conform to the created 3D computer model of the device.

Disclosed is an exemplary protection device for an animal comprising a sleeve made of stretchable fabric configured to slip on/off the animal's head having an inside surface, a pair of passive noise reduction components disposed on the inside surface of the sleeve and configured to form a seal with the surface of each external ear of the animal when the sleeve is installed on the animal's head, and a drawstring for removably tightening the sleeve to the animal's neck to create the seal between each of the noise reduction components and the surface of each of the animal's external ear wherein the inside surface of the sleeve is in contact with the animal's head when the sleeve is installed. The device may be designed for an animal comprising at least one of military working dogs, hunting dogs, cats, and horses.

Disclosed is a hearing protection device for a dog comprising a sleeve made of stretchable fabric configured to slip on/off the dog's head and having an inside surface, a pair of passive molded noise reduction components made of liquid silicone rubber and disposed on the inside surface of the sleeve and each configured to form a seal with the surface of an external ear of the dog when the sleeve is installed on the dog's head, and a drawstring for removably tightening the sleeve to the dog's neck to create the seal between each of the noise reduction components and the surface of each of the dog's external ear wherein the inside surface of the sleeve is in contact with the dog's head when the sleeve is installed. Each molded noise reduction component may comprise an internal surface comprising a cup-shaped structure bounded by a ring wherein the ring is configured to seal with each external ear surface of the dog, and a planar external surface disposed opposite to the internal surface wherein each of the internal and external surface comprises an arch-shaped end disposed opposite to a straight end. The thickness of the molded noise reduction component at the straight end is preferably greater than the thickness at the arch-shaped end. The device may be characterized by a noise reduction of between about 20 dB and about 30 dB at noise frequencies of between about 1000 Hz and about 2000 Hz.

Disclosed is an exemplary method for fabricating a molded noise reduction component comprising selecting a liquid silicone rubber material (LSR) characterized by a mixed viscosity of about 3000 cps prior to curing, degassing the mixed LSR material by exposing the material to a vacuum, feeding the degassed LSR material into a mold of predetermined shape and curing the degassed LSR material. The vacuum level during the degassing step may be between about 10 mm Hg and 50 mm Hg. The curing step may comprises holding the degassed LSR material for about 4 h at ambient room temperature, holding the material at about 80° C. for about 2 h, and holding the material at about 100° C. for about 1 h. The mold may be made of Aluminum 6061 Alloy.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1. Sound levels for military noise sources: continuous noise sources (empty bars) and impulse noise sources (hashed bars).

FIG. 2. Canine hearing threshold for left and right ears.

FIG. 3. Typical performance of passive noise reduction devices. Takeoff noise of a Cessna 172RG Cutlass airplane (top). Noise reduction by passive devices (bottom).

FIG. 4. Improved low frequency noise reduction using ANC for C-130 aircraft landing noise. With ANC-off (top) and with ANC-on (bottom).

Figure 8:
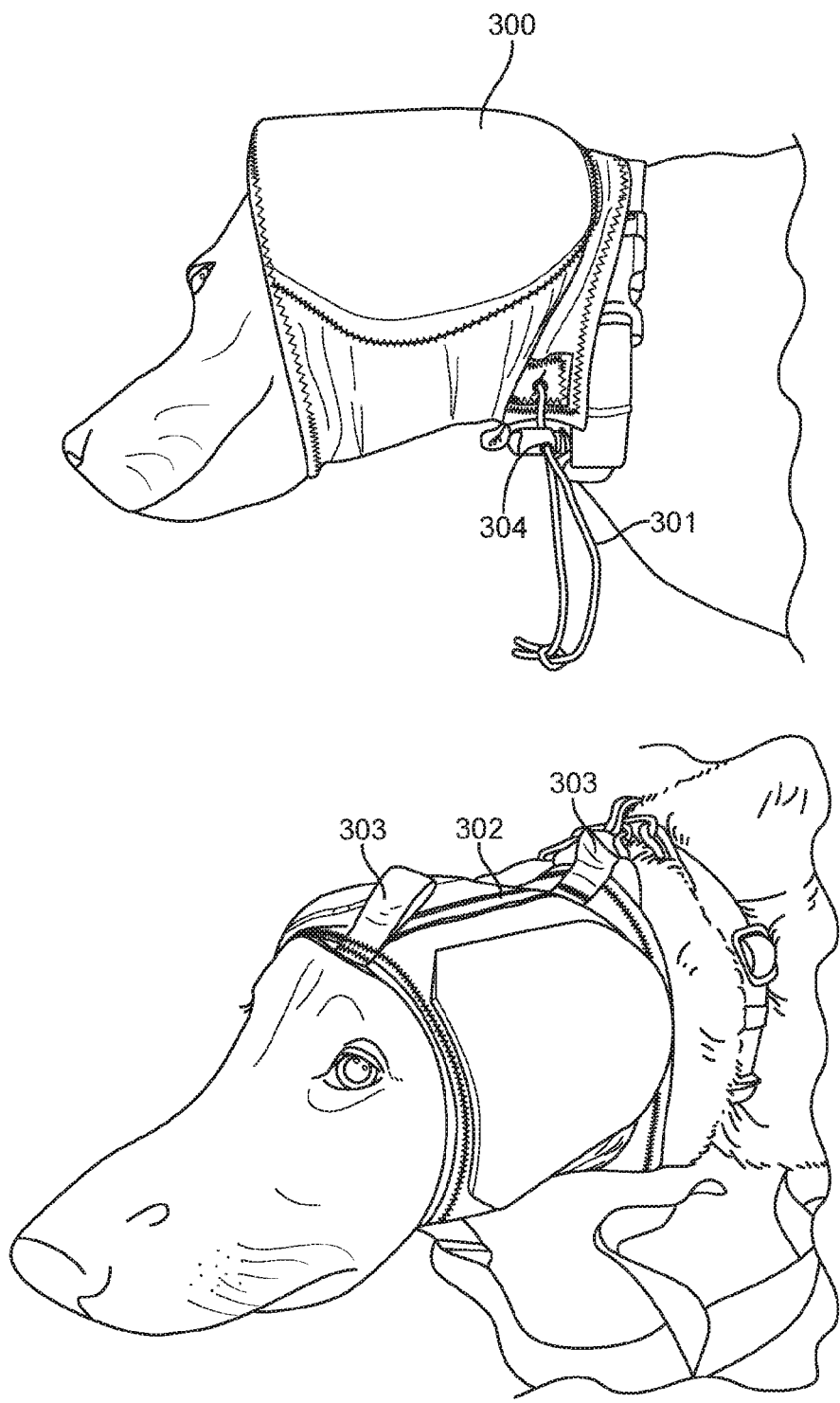

FIG. 8. Perspective views of a dog wearing an exemplary hearing protection device.

Figure 9:
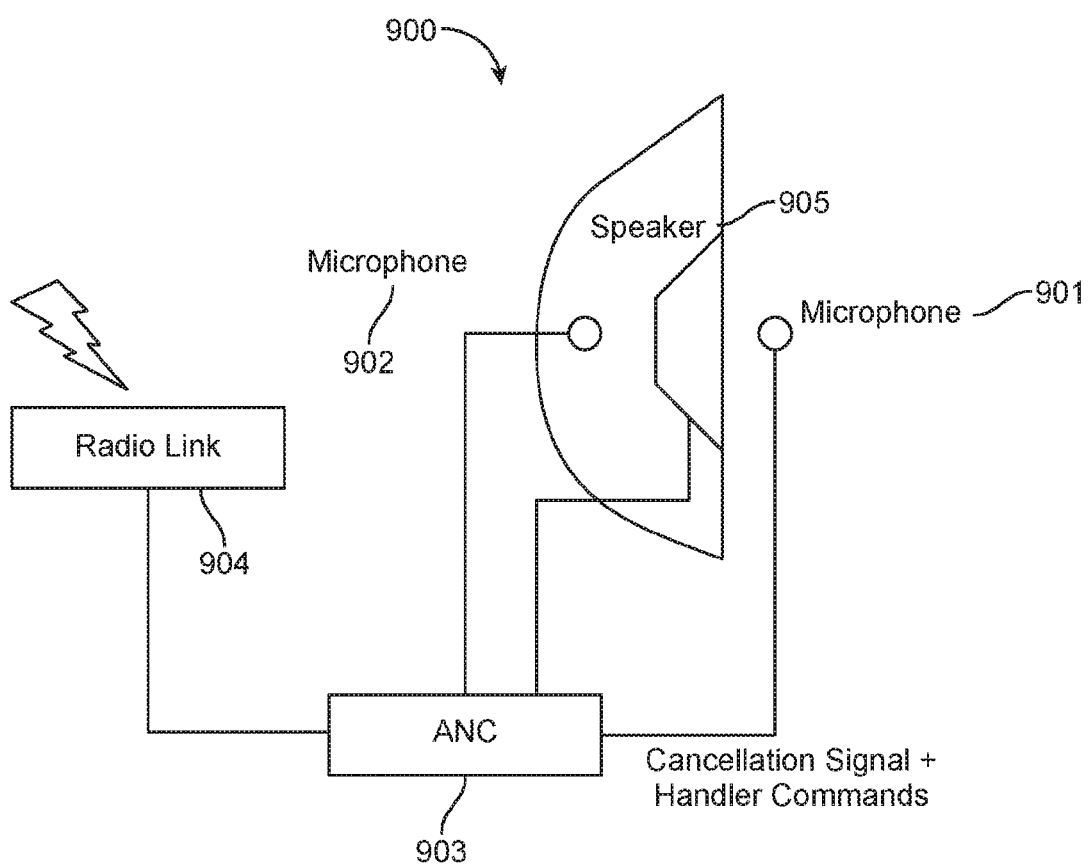

FIG. 9. Schematic diagram of an active noise cancellation subsystem.

Figure 10A:
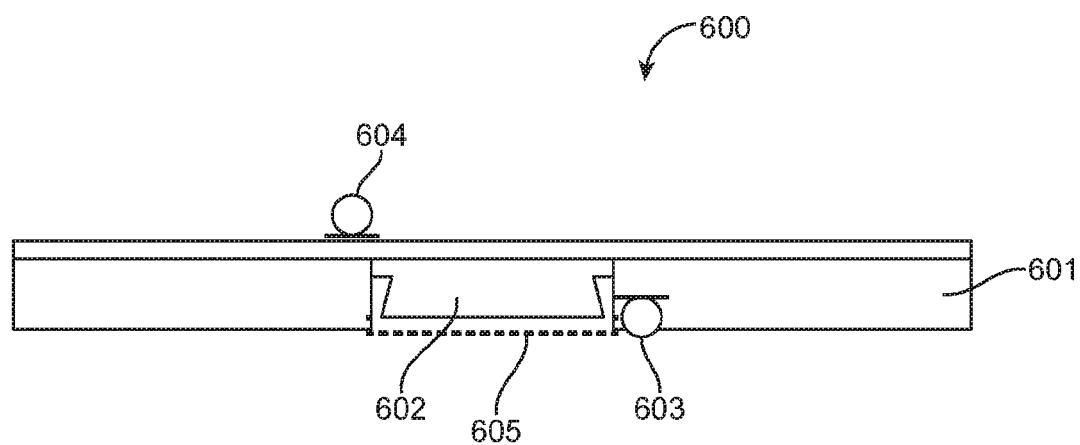
Figure 10B:
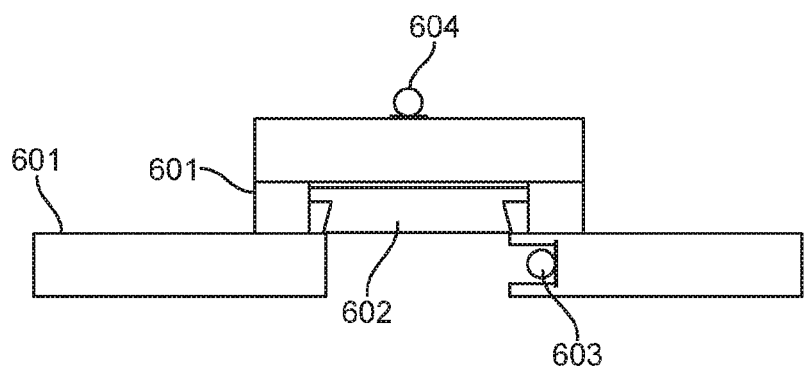

FIGS. 10A and 10B depict a schematic diagram of exemplary noise reduction components in an exemplary hearing protection device having a slim design, and a schematic diagram of exemplary noise reduction components in an exemplary hearing protection device having a design providing enhanced noise reduction, respectively.

Figure 11:
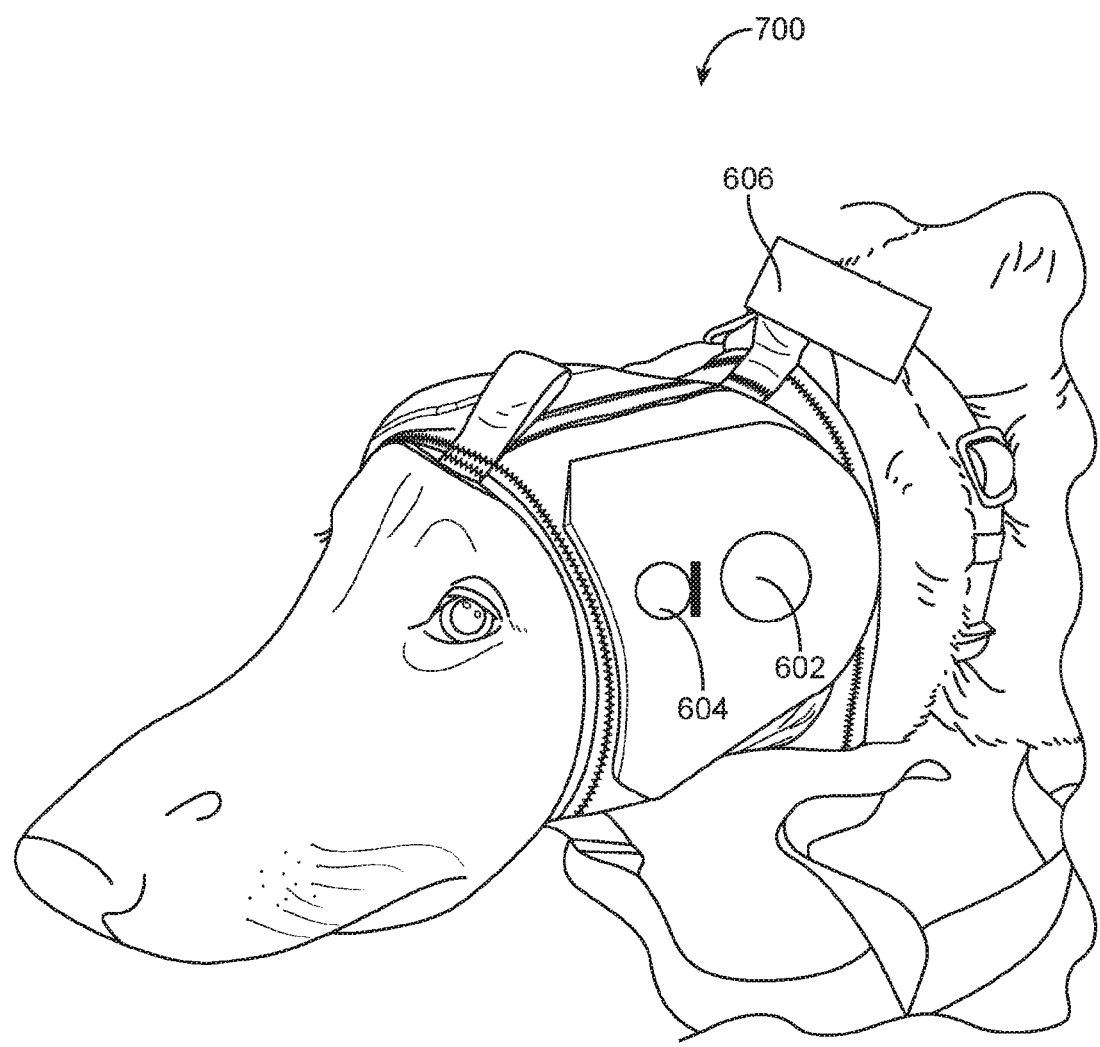

FIG. 11. Perspective view of a dog wearing an exemplary hearing protection device with ANC capabilities showing location of external microphone, speaker, and control module and power supply.

Figure 12:
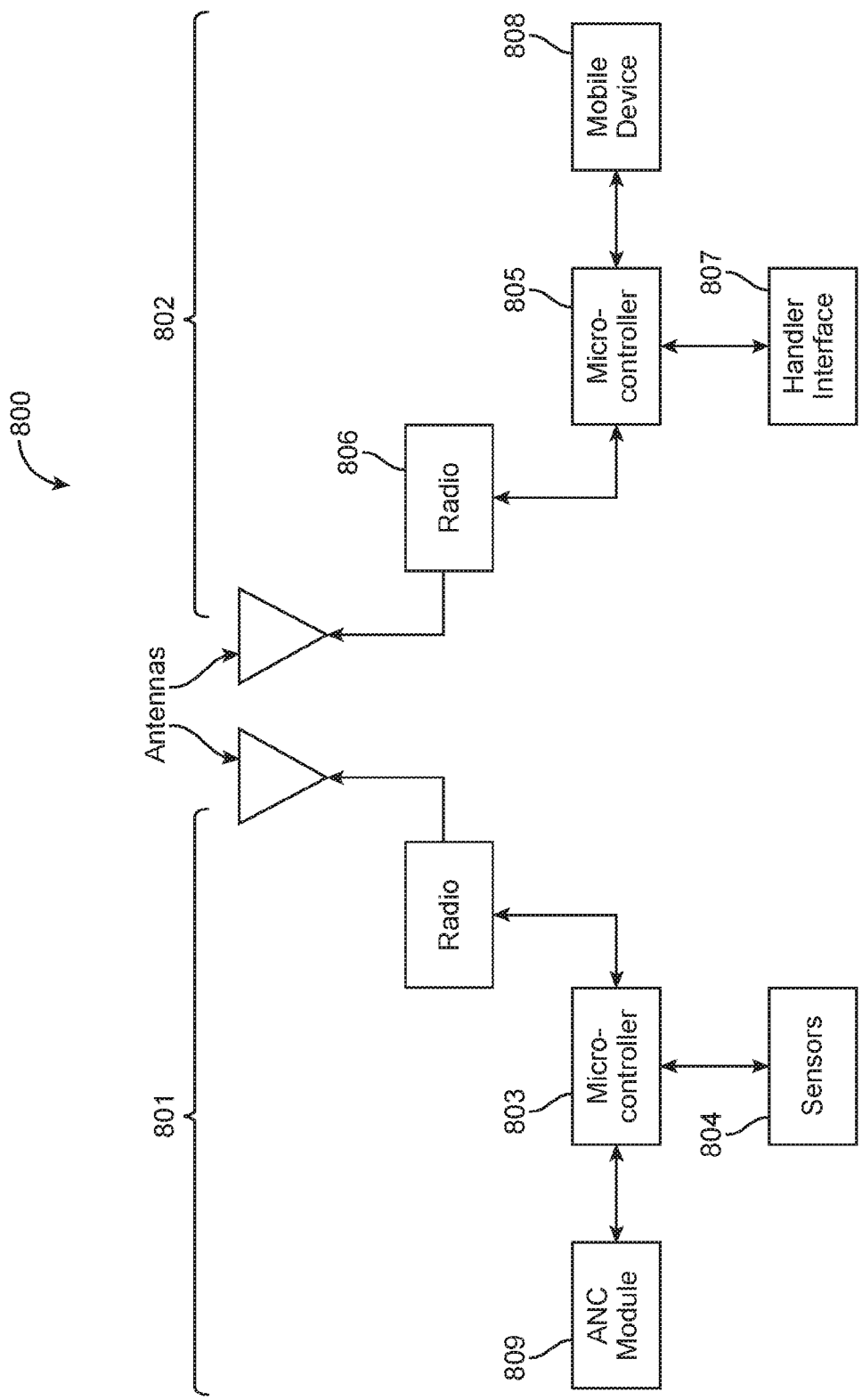

FIG. 12. Schematic diagram of an exemplary communication component for an exemplary hearing protection device.

FIGS. 13A, 13B, 13C depict perspective views, internal surface view, and external surface view of an exemplary molded noise reduction component for use in an exemplary hearing protection device, respectively.

Figure 14:
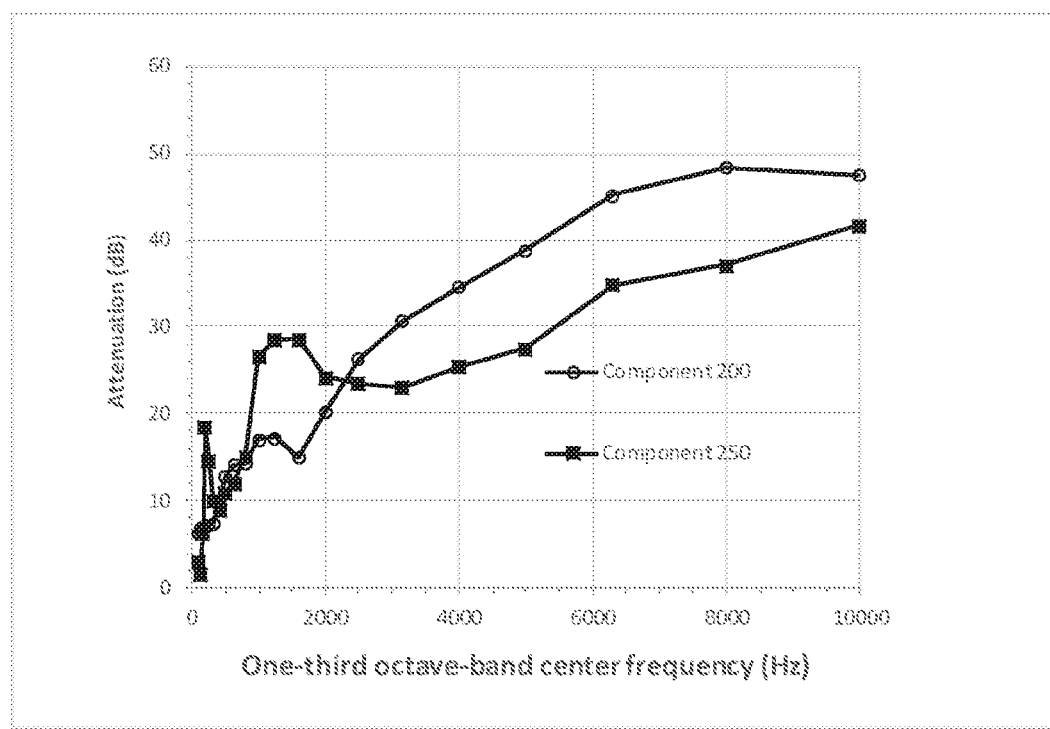

FIG. 14 shows noise attenuation measured using an exemplary composite noise reduction component and an exemplary molded noise reduction component at various input noise frequencies.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the pilot assembly and methods may be practiced. These embodiments, which are to be understood as "examples" or "options," are described in enough detail to enable those skilled in the art to practice the present invention. The embodiments may be combined, other embodiments may be utilized or structural or logical changes may be made without departing from the scope of the invention. The following detailed description is, therefore, not to be taken in a limiting sense and the scope of the invention is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. For construing the scope of the term "about," the error bounds associated with the values (dimensions, operating conditions etc.) disclosed is ±10% of the values indicated in this disclosure. Unless otherwise specified, the word "substantially" used before a specific word includes the meanings "considerable in extent to that which is specified," and "largely but not wholly that which is specified." In addition, "sound" and "noise" may be interchangeably used.

DETAILED DISCLOSURE

Particular aspects of the invention are described below in considerable detail for the purpose for illustrating its principles and operation. However, various modifications may be made, and the scope of the invention is not limited to the exemplary aspects described.

Figure 1:
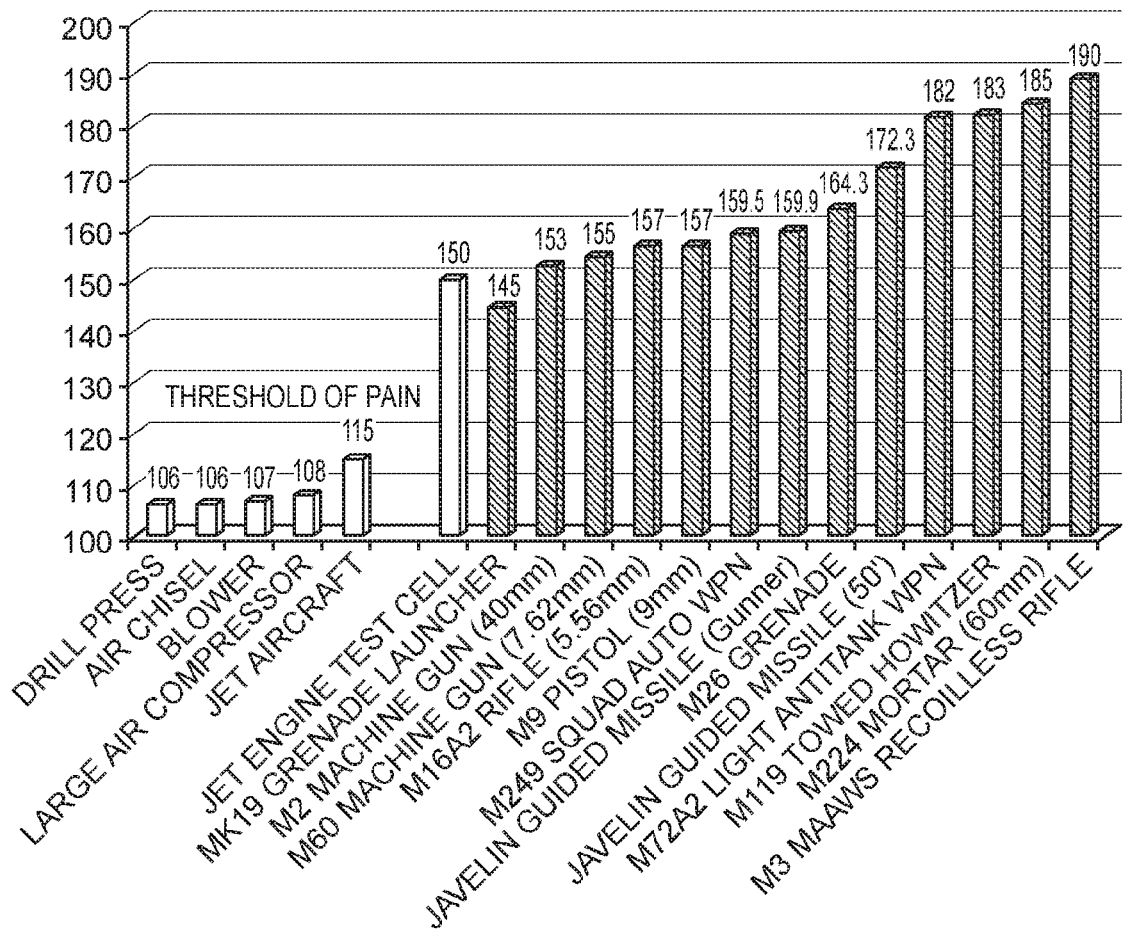
Figure 2:
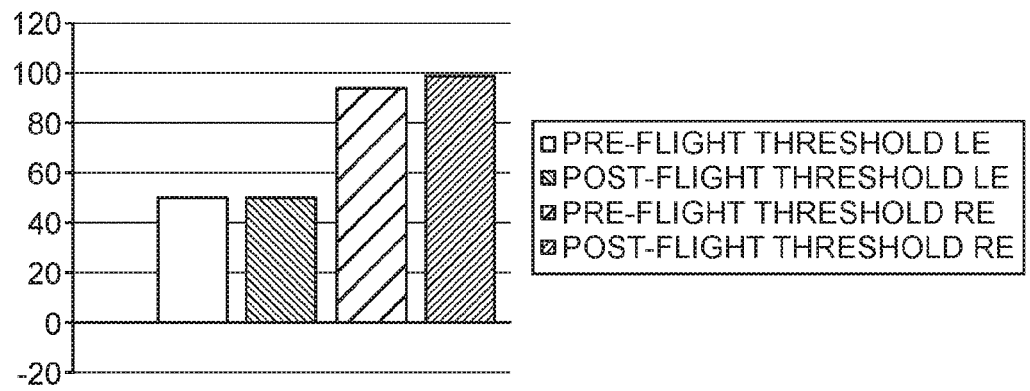
Figure 3:
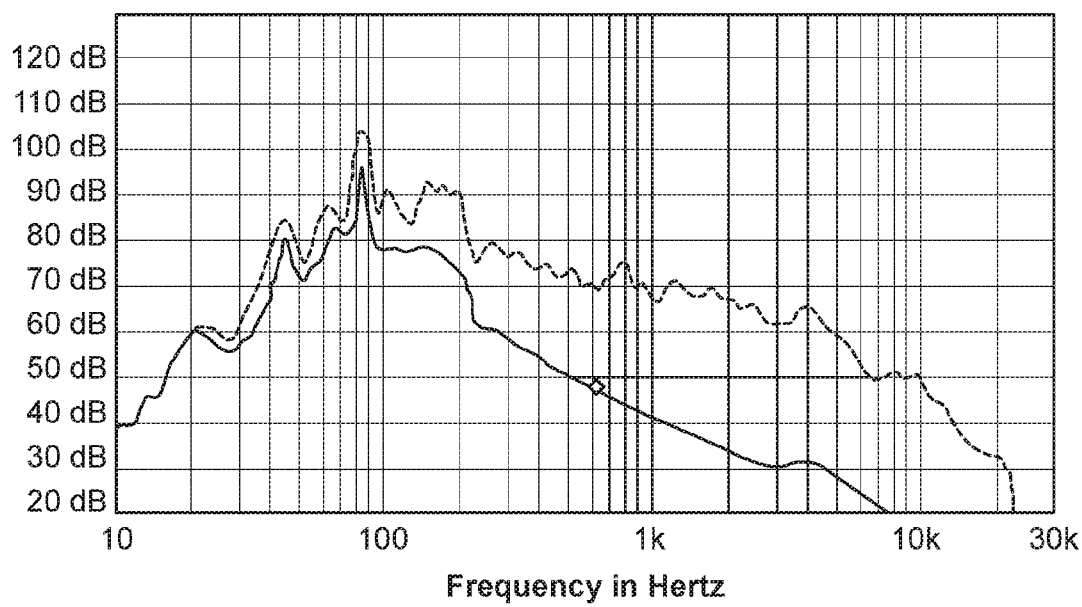
Figure 4:
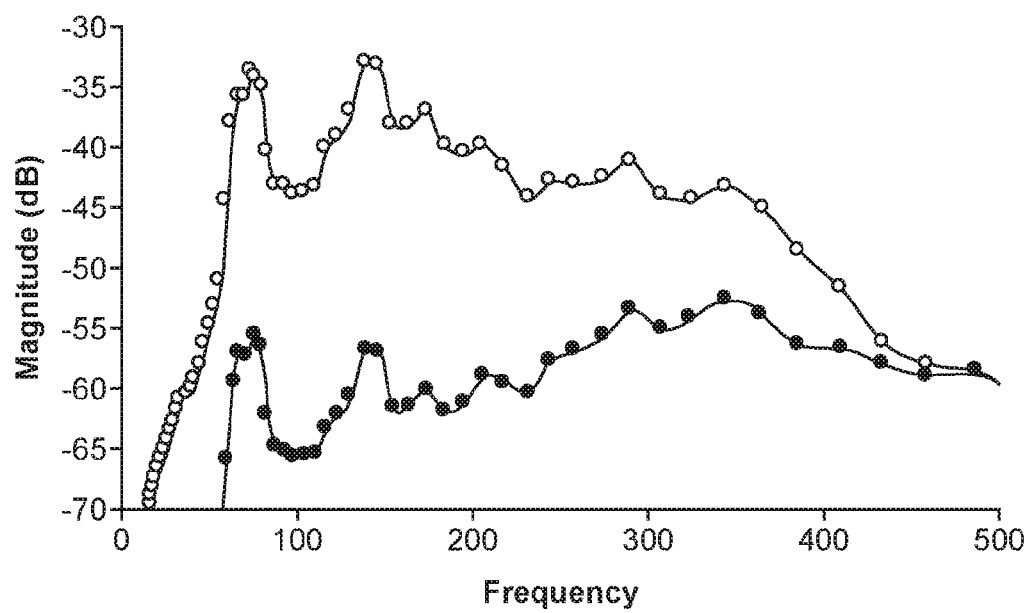
Figure 5A:
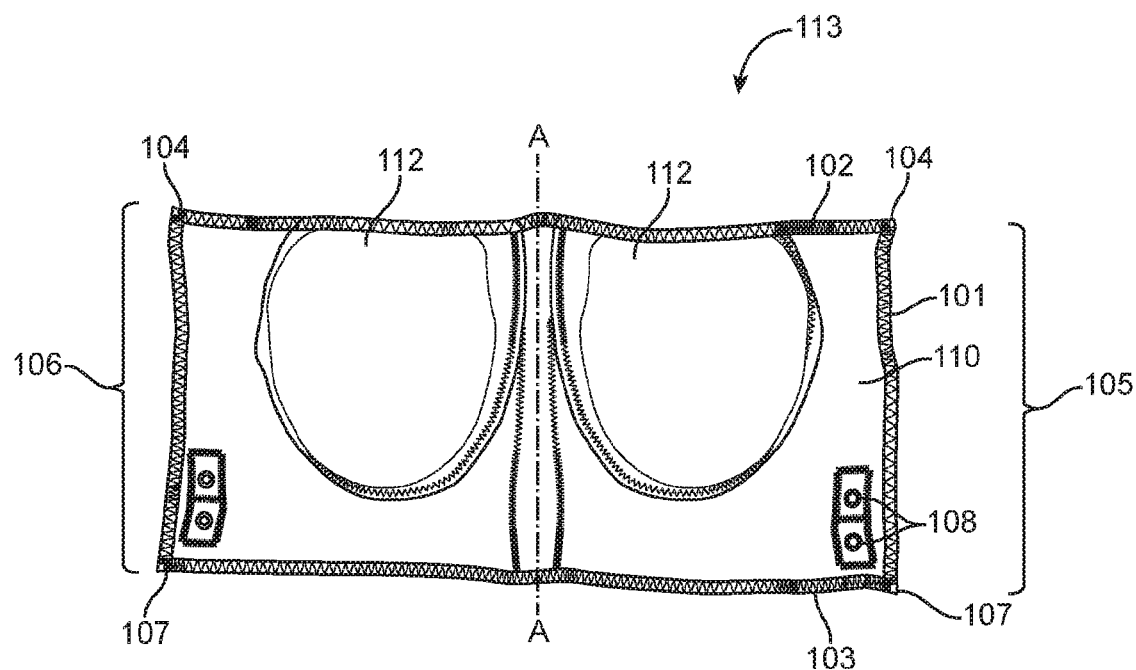
FIGS. 5A and 5B depict a top view of the inside surface of an exemplary partially assembled hearing protection device, and a top view of the outside surface of an exemplary partially assembled hearing protection device, respectively.
Figure 5B:
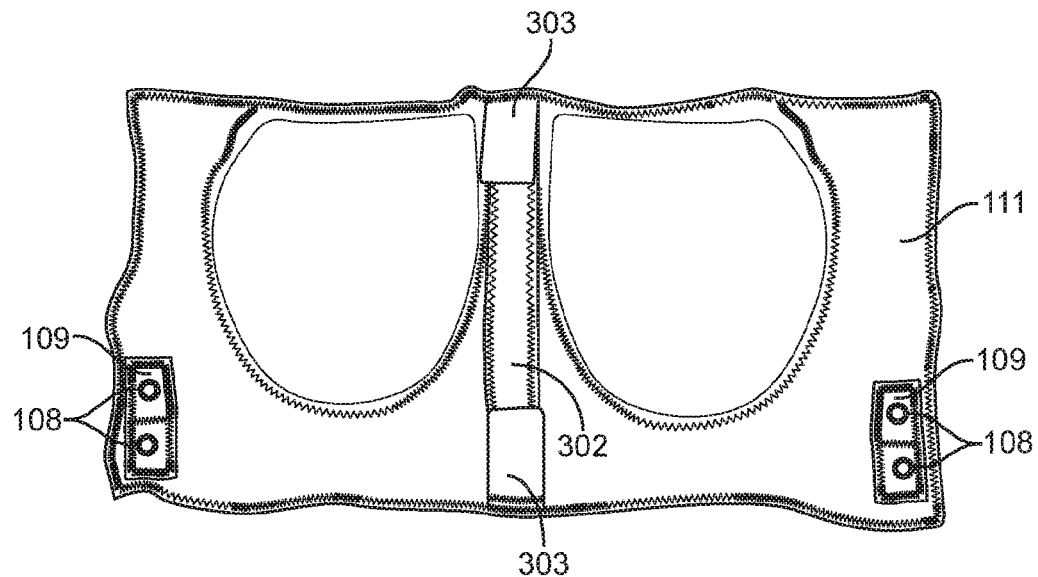
Figure 6A:
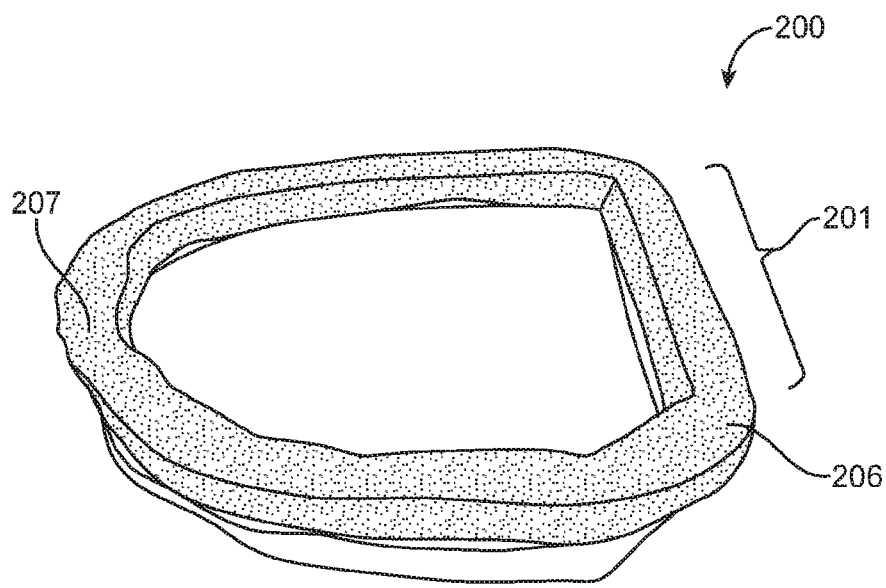
FIGS. 6A and 6B depict a perspective view of an exemplary noise reduction component for use in an exemplary hearing protection device showing the soft foam compressible ring, and perspective view of an exemplary noise reduction component for use in an exemplary hearing protection device showing the MLV barrier, respectively.
Figure 6B:
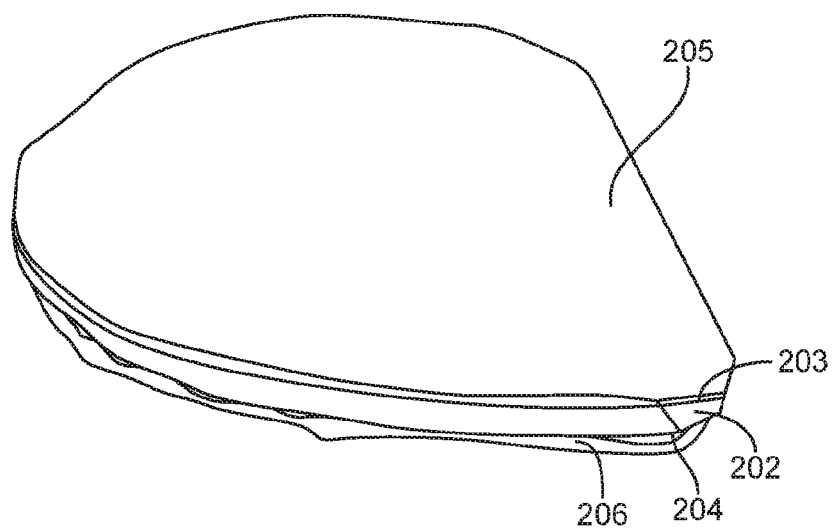

An exemplary hearing protection device 113 (FIGS. 5A and 5B) may comprise a sleeve 100 preferably made of a stretchable fabric material piece 101 and may be substantially rectangular in shape. Piece 101 has top edge 102 and a bottom edge 103. Edge 102 extends between top corners 104. Edges 102 and 103 are disposed substantially parallel and opposite to other and joined by a first end 105 and second end 106 which are disposed on either side of a center line AA. Piece 101 further comprises a plurality of holes disposed near each bottom edge corner 107 to receive grommets 108 through which an adjustable drawstring may be inserted. The holes and grommets may be reinforced with second material 109 that is relatively rigid compared to stretchable fabric piece 101. Noise reduction components 200 (FIG. 6) are disposed on either side of a centre line AA and substantially equidistant from the center line AA on the inside surface 110 of sleeve 100, with a linear edge 201 substantially aligned with top edge 102. Inside surface 110 of sleeve 100 is in contact with the dog's skin and outside surface 111 is the surface of sleeve 100 that is exposed to the atmosphere. The shape and size of noise reduction components 200 may be varied depending on the size and shape of a dog's external ear (or pinna) and the shape and size of the dog's head.

Noise reduction component 200 may be enclosed in a space between piece 101 and a housing cover 112, which is suitably joined to piece 101. Cover 112 may be made of acoustic speaker grill cloth material (e.g., as supplied by Acoustical Solutions, VA). The grill cloth material is typically mildew resistant and approved for outdoor use. For example, housing cover 112 may be sewn to piece 101. Alternately, housing cover 112 may be configured as a pouch, with one side open and the other sides of the pouch joined (sewn or otherwise sealed) to piece 101. Component 200 may then be inserted the pouch through the open side. The open side of the pouch, for example, may be disposed along edge 102, and may then be sealed or joined by sewing or other suitable means.

Each noise reduction component 200 is a soft ear muff and may comprise a composite structure formed using a plurality of foam materials and is preferably sized to substantially cover the external ear of a dog. Component 200 may comprise a first foam section 202 (FIG. 6B) having a first surface 203 and second surface 204. Section 202 may be between about 0.4 in. and about 0.5 in. in thickness and preferably between about 0.425 in. and 0.475 in. in thickness. Section 202 is preferably a polymeric closed cell foam acoustic barrier material with a barium infused mass loaded vinyl (MLV, poly vinyl chloride or PVC) backing material 205 (FIG. 6B), that include but are not limited to the LuxuryLiner Pro™ supplied by Second Skin Audio (Tucson, AZ) and Quiet Barrier™ supplied by Soundproofcow (Chambersburg, PA). The weight/area ratio of the MLV materials may vary between about 1 lb/ft$^2$ and about 2 lb/ft$^2$. MLV barriers may be composed of salts, sands and tiny metal particles that yield sound reducing properties similar to lead materials. These highly dense materials block sound waves. Surface 203 may be joined (e.g. glued) to the backing material layer 205. The backing material layer 205 may be between about 0.05 in. and 0.15 in. in thickness and preferably between about 0.07 in. and about 0.12 in. in thickness. Component 200 may also comprise a compressible second foam section 206 (FIG. 6A) preferably configured in the shape of a ring that is aligned with the shape of foam section 202. Section 206 is preferably a compressible polymeric closed cell foam material such as OverKill Pro™ (vinyl infused closed cell foam) supplied by Second Skin Audio (Tucson, AZ). The weight per unit area ratio is preferably between about 0.2 lb/ft$^2$ and about 0.25 lb/ft$^2$. In a closed cell foam, each cell does not interconnect with other cells. Examples of polymeric closed cell foam materials include EPDM (ethylene propylene diene monomer), neoprene, chloroprene rubber (CR) comprising polymers with densities ranging from about 5 lb/ft$^3$ and about 7 lb/ft$^3$. Closed cell foam materials are ideal for sealing purposes. Compressible foam material 206 helps to create a seal between component 200 and the surface of the dog's external ear when sleeve 100 is installed on the dogs' head (FIG. 8). Section 206 may be joined (e.g. glued or joined using double stick tape) to section 202 along the edges of surface 204. The thickness of foam section 206 is substantially similar to that of section 202. Assembled component 200 as described above may be between about 0.65 in. and about 1.1 in. in thickness and is preferably between about 0.8 in. and about 1.0 in. in thickness. Component 200 is housed in sleeve 100 such that ring-shaped surface 207 of section 206 is in contact with housing cover 112 and subsequently forms a seal with the surface of the dog's ear. Exemplary device 113 with noise reduction component 200 therefore conforms to the shape of the dog's head and external ear and flexible sleeve 100 distributes pressure more uniformly, minimizes peak pressure points on the dog's head. Device 113 therefore provides superior noise reduction capabilities without irritating the dog or dislodging from the dog's ear and breaking the seal between the device and the ear compared to commercially available devices. Device 113 is conformable to wide variations in the shape and size of the dog's head and dog's external ear and provides a reliable seal between the noise reduction component and the dog's ear. Vinyl backing layer 205 may also be provided along the sides of component 200 to cover the exposed surfaces of foam sections 202 and 206 to further improve noise reduction. That is, in addition to covering surface 203, vinyl layer 205 may be used to cover all exposed areas of component 200 except surface 207.

Figure 7A:
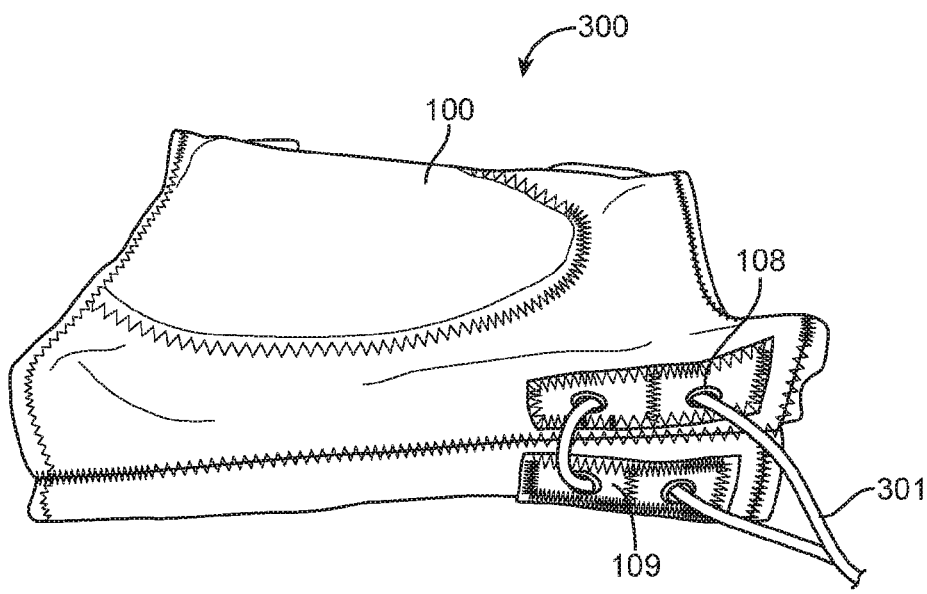
FIGS. 7A and 7B depict a perspective view of an exemplary assembled hearing protection device showing the seam of the sleeve, and a perspective view of an exemplary assembled hearing protection device showing the reinforcing wear strip, respectively.
Figure 7B:
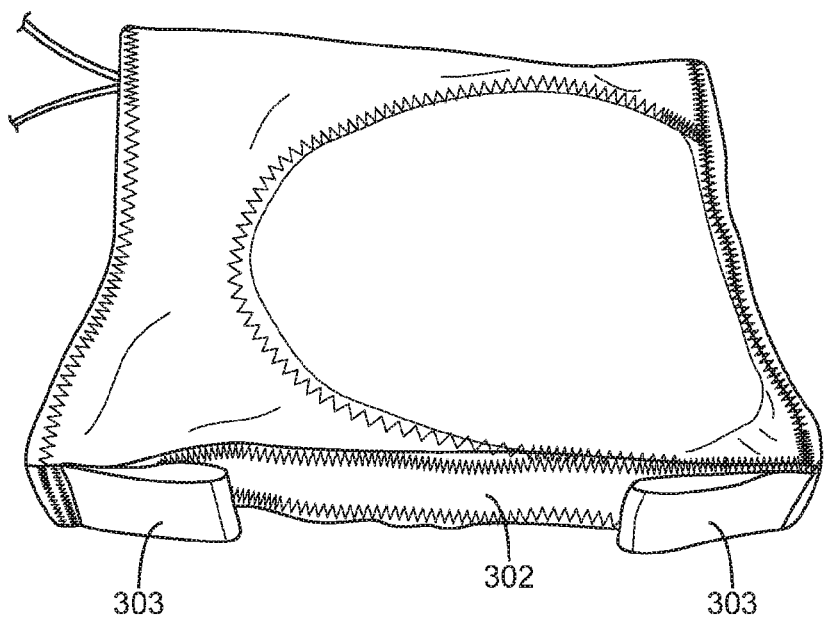

Exemplary hearing protection device 300 may be assembled by folding piece 101 over center line AA (after installing the noise reduction components 200 in place) and joining edges 105 and 106. Preferably, a substantial length of edges 105 and 106 are sewn together using commonly known "stich-in-the ditch" techniques and the like. As shown in FIG. 7A, edges 105 and 106 are joined (by sewing)

from top corners 104 to about a section just above the top of reinforcing material 109. Preferably, about 60% to about 70% of the length of edges 105 and 106 from top corners 104 is joined in a seam. The un-joined length section of edges 113 enables easy donning (putting on) and doffing (taking off) the sleeve 100. After donning, the unsewn sections of edges 104 and 105 may be removably joined using drawstring 301 (FIG. 7A) that is inserted through grommets 108. Drawstring 301 may be loosened or tightened as required with the help of using a spring-loaded stop-cord lock 304. To prevent fraying or tearing of material 101 along center line AA during repeated donning and doffing, reinforcing wear strip 302 (FIG. 7B) may be joined to the outside surface 111 of sleeve 100 along (or substantially about) center line AA and extending substantially between top edge 102 and bottom edge 103. Donning and doffing tabs 303 are joined to strip 302 and piece 101 such that they lie between edges 102 and 103 away from the sight of the dog and to avoid distracting the dog. Strip 302 is not joined to the inside surface of piece 101 to minimize any opportunity to cause irritation and distraction to the dog.

With drawstring 301 in a loosened state, exemplary device 300 may be slipped over the dog's jaws (and muzzle if the dog is muzzled) such that drawstring 301 is under the dog's chin. (FIG. 8). The sleeve is installed over the dog's cranium to ensure that the dog's ears are covered by noise reduction components 200 and sealed using compressible foam section 206. Drawstring 301 is tightened and locked (held in place) using stop-cord spring loaded lock 304. Exemplary device 300 forms a seal between the noise reduction component and the external surface of the dog's ear and is therefore held in place sealing the dog's ear even when the dog runs through bushes (e.g. when a dog is used for hunting purposes) or is in an active state. Exemplary hearing protection device 300 eliminates the need to tightly wrap a stretchable material around the head of a dog without realizing appreciable hearing protection as described in International Patent Pub. No. WO2009134863. When the device needs to be removed, the drawstring is loosened, and the device is slipped off the dog's head.

In exemplary device 113, material piece 101 is preferably between about 15 in. and about 17 in. in length and between about 8 in. and about 10 in. in width. Device 113 with these dimensions is suitable for providing sound protection for adult Malinois dogs with weight between about 64 lb to about 75 lb for male dogs and between about 55 lb and about 66 lb for female dogs. When edges 105 and 106 are joined as previously described, the length dimension of sleeve 100 (or material 101) constitutes the circumference of sleeve 100. Stretchable material piece 101 may be woven or knit. Piece 101 may be made of elastane containing elastomeric materials such as spandex and the like (e.g. LYCRA® brand). Elastane content in the fabric may vary between 1% and 15%. Breathable and fast drying materials including, but not limited to Supplex (supplied by Invista) and Durastretch® Coyote (supplied by Outdoor Wilderness Fabrics Inc.) may also be used. These materials stretch lengthwise and crosswise, that is, they provide a 4-way stretch. Spandex, for example, may be stretched repeatedly and recover to its original length and shape. It can elongate to over 500% its length-at-rest without breaking. It is also lightweight and provides for both comfort and fit. It is easily washable, is abrasion resistant, and has a long life. The Durastretch material may comprise about 66% nylon and about 34% spandex and is a lightweight, durable fabric with superior abrasion resistance. Preferably, the sleeve material comprises between about 60% to about 70% nylon and between about 30% and about 40% spandex. Most preferably, the sleeve material comprises about 65% to about 70% nylon, with the remaining being spandex. Device 300 (including components 200) is lightweight and may weigh between about 200 g and about 300 g and preferably between about 200 g and about 250 g. Device 113 may be capable of providing noise reduction of about 20 dBA to about 30 dBA (measured on a A-weighted scale) using noise reducing components 200. In the A-weighted scale, the decibel values of sounds at low frequencies are reduced, compared with unweighted decibels, in which no correction is made for audio frequency. This correction is made because the human ear is less sensitive at low audio frequencies, especially below 1000 Hz, than at high audio frequencies. Preferably, piece 101 is made of a material that has high elasticity and high thermal conductivity.

The dimensions of exemplary sleeve 100 may be changed depending on the size and breed of the dog. For dogs with larger pinna, a larger volume inside of the cup may be used to increase comfort by reducing pressure on sensitive ear tissue. The dimensions may be changed such that sleeve 100 is configurable to provide hearing protection for any type of dog including military working dogs, hunting dogs and other animals that include, but are not limited to cats and horses.

Disclosed is an exemplary method for hearing protection for a dog comprising attenuating external noise levels using device 113, which may comprise slipping an exemplary hearing protection device on to the dog's head, aligning each of the passive noise reduction components with each of the dog's external ear, and removably tightening the device by adjusting the drawstring to create a seal between each of the noise reduction component and the each of the dog's external ear wherein the inside surface is in contact with the dog's head when the sleeve is installed.

Disclosed is an exemplary method to enable a user to order a fit-for purpose hearing protective sleeve as disclosed herein using an exemplary "app" that is configured to use user-provided information for designing and fabricating the sleeve. The "app" may also require the user to register and transmit a user's contact details, payment details, and the like. A mobile application software or "app" is a computer program configured to run on a mobile device such as a smart phone, tablet or watch. An app comprises a front-end component or user interface ("UI") and is designed to provide the user with an easy-to-use and friendly interface. The front end communicates with a back-end component which facilitates data routing, security, authentication, authorization, working off-line, and service orchestration. An app may also communicate with one or more intermediate or middle components including, but not limited to, mobile app servers, message queuing, enterprise service bus ("ESB") and other service-oriented architecture ("SOA") infrastructure components. Data synchronization between the mobile device and a database or cloud and offline (without internet connection) capabilities are key to the seamless functioning of successful mobile apps. Providers of database and cloud services such as Couchbase Mobile (Couchbase), Azure Mobile Services (Microsoft), Cognito (Amazon), Firebase (Google) offer synchronization and offline capabilities with their mobile offerings. The app should preferably provide for secure data access communication with synchronized and decentralized storage, transmission and storage using features such as address authentication, data at rest, which relates to whether the app supports file system encryption and data-level encryption, data in motion, and read/write access that defines what data may be accessed and changed/modified by users. Databases may be relational (SQL databases such as Oracle, mySQL) or NoSQL (e.g. MongoDB, CouchDB). Further, for decentralized data writes on mobile platforms, the same data can be simultaneously modified on multiple devices and may create a conflict between data access from multiple devices. The app should preferably incorporate a mechanism for resolving those conflicts. The conflict resolution mechanism may allow resolution automatically, on the device, in the cloud, or could be manually initiated.

Once downloaded to a mobile device, the app may prompt the user to create a user account and then may prompt the user to:

(a) enter the dog's breed;
(b) enter the dog's age;
(c) enter any other details related to the environment to which the dog would be exposed to, for example, including but not limited to environmental noise decibels levels and frequency;
(d) take photographs or videos of the dog from several perspectives that would enable a supplier of a hearing protection sleeve or any hearing protection device to calculate details that include but are not limited to: (i) height of the pinnae, (ii) width of the pinnae, (iii) circumference of the head, and (iv) size of the head;
(e) enter shipping details; and the like.

The collected information may be processed to determine at least one of the size of the device, the structure and size of the noise reduction component, and whether at least one of passive noise reduction bypass and active noise cancelling is required. A 3D computer model of the dog's head and the device using the collected and processed information may be developed using solid modeling CAD packages such as SolidWorks and the like for testing the fit of the device. The custom device may then be fabricated to substantially conform to the created 3D computer model of the device.

Impulse noise levels from small arms, artillery and mortar fire can exceed 180 dB, which is well above the dynamic range and peak values (typically <120-130 dB) of available miniature microphones. While passive hearing protection can be used to prevent damaging sound levels from being transmitted to the dog, it is desirable that the dog be able to hear other sounds, such as commands from the owner/dog handler. In addition, such high noise levels can saturate the microphone of an electronic control system and result in the system becoming unstable or ineffective. A microphone external to the hearing protector can sense signals and process them to remove unwanted sounds and use a speaker or other sound source internal to the hearing protector to playback desired sounds. For example, a detector can be used to identify an explosion or other high-level noise and block all sound. This will prevent high level noise from saturating the system and causing loud or damaging sounds from being played back. Other filters can be used to limit playback to a fixed level or bandpass and/or speech filtering to extract desired sounds. In addition, a microphone internal to the hearing protection device may be extrapolated to infer impulse peak exposure levels and used to alert the operator to the level of effectiveness of the dogs hearing protection.

Exemplary hearing protection device 113 may be modified to provide active noise control ("ANC") at low noise frequencies of 100 to 1000 Hz. The entire disclosures of U.S. Pat. No. 9,654,854 entitled "In-ear device incorporating active noise reduction," U.S. Pat. No. 6,278,786 entitled "Active noise cancellation aircraft headset system," U.S. Pat. Pub. No. 2015/0294662 entitled "Selective Noise-Cancelling Earphone," U.S. Pat. Pub. No. 2012/0014532 entitled "Noise Canceling Headphone," U.S. Pat. No. 7,058,368 entitled "Adaptive feedforward noise cancellation circuit," U.S. Pat. Pub. No. 2002/0141599 entitled "Active noise canceling headset and devices with selective noise suppression," are incorporated by reference herein in their entireties.

ANC components in a hearing protective device for a dog may comprise: (1) a feedback component for noise/anti-noise generation, which is preferably optimized for a dog's hearing range. Adaptive digital processing or analog processing algorithms are comparable to that used in ANC systems for human use, and (2) a feedforward component to sense loud impulse noise using an external microphone and shut off ANC. When ANC is turned off, noise attenuation is achieved by passive mode. Unlike ANC systems suitable for human use, in canine (e.g. MWD) hearing protection systems, the feedforward signal may be out of the range of normal human hearing and may allow a handler to communicate acoustically with the dog (e.g. use a dog whistle) without compromising the effectiveness of the noise reduction. Alternately, pre-recorded commands, for example, a command that makes the dog to sit and stay still, may be transmitted to the animal triggered by shut-off of the ANC components due to an impulse noise. FIG. 9 is a schematic diagram of components 900 required to provide ANC capability. An internal residual noise microphone 901 is used to measure noise levels in proximity to the tympanic membrane in the ear while an external microphone 902 is used to measure external noise and may be located internal or external to the headset. The ANC controller 903 uses feedback to calculate an inverse signal proportional to the noise, which is sent to speaker 905. Using 902, the ANC controller may also use a feedforward approach to produce cancelling signals or mix desired sounds. Sound from the speaker (anti-noise) mixes with the noise to produce the noise reduction effect. For low frequency noise, the correlation time of the noise signal is significantly greater than the delay of the electronics and the transfer function is stable over time. Most commercially available ANC headsets utilize this approach, typically using analog electronics for low cost and power consumption. Characteristics of the dog's ear may introduce complexities that may require adaptive digital signal processing. The feed forward microphone 902 detects loud impulse noises and stop operation of the ANC controller. Under these conditions, noise attenuation may be achieved using the passive components of the hearing system. Further, the ANC controller may compress sound during intervals when the handler is communicating with the canine. As with the feedback system, this can be implemented with analog electronics. An ANC controller 903 that combines feed forward and feed-back modes may improve performance over only feedback mode and may require the use of a digital control system.

Exemplary passive noise reduction component 200 may be modified to provide ANC capabilities using such that ANC components that comprise an internal microphone, external microphone, and speaker. Similar to component 200, exemplary noise reduction soft muff component 600 (FIG. 10A) may comprise a foam section 601 preferably made of closed cell foam acoustic barrier material with a barium infused mass loaded vinyl (poly vinyl chloride or PVC) backing material such as the LuxuryLiner Pro™ supplied by Second Skin Audio (Tucson, AZ). Alternatively, a molded soft muff (cup) as previously described, may incorporate a speaker. However, in component 600, foam section 601 may be configured to substantially house ANC components speaker 602 and internal microphone 603, which along with external microphone 604 provide ANC capability as previously described. "Substantially housed" means that certain components such as wiring that connects ANC components to electronics module 606 may extend out of foam section 601. The thickness of the foam may be varied to house components 602 and 603. In addition, speaker 602 may be protected by grill 605. Modified noise reduction component 600 may then be housed within cover 112 of sleeve 100 to yield an exemplary noise reduction device 700 with ANC capabilities. (FIG. 11). An electronic control module and power supply 606 supported by a suitable harness may be located on the back of the dog to provide power and run/operate the ANC components to provide ANC capability. ANC capability may be turned on/off using module 606 by the dog's handler. Electronics module 606 may be mounted on the dog's collar as shown or may be suitably attached to sleeve 100. Internal microphone 603 and cabling between the microphones, speaker and electronics module are not shown in FIG. 11. Further, component 600 may be modified to improve passive noise reduction capabilities by increasing the surface area of foam section 601 as shown in FIG. 10B. Passive hearing protection does not discriminate between desired and undesired sound and effectively disrupts any communication with the handler. Although hand or other visual signals may help, in many situations they are of only limited applicability. Components such as the external microphone, speaker, and control module may be used for both passive noise reduction electronic bypass as previously described, and ANC.

Further, it may be essential for the dog's handler be able to communicate with the working dog in high noise environments. In an exemplary, hearing protection and communication device for animals such as military working dogs or hunting dogs, exemplary hearing protection device 700 may be modified to provide at least one of active noise cancellation for communication between the handler and the MWD. A combination of passive and active noise cancellation components as previously described herein may provide noise attenuation across the entire acoustic spectrum and reach 30 dB to 40 dB of noise reduction across the canine hearing range. Exemplary communication system (or component) 800 may comprise dog module 801 and a handler module 802 as shown in FIG. 12. In dog module 801, microcontroller 803 may detect and block impulsive sounds that would saturate the microphones. Microcontroller 803 may also collect and transmit information from other sensors (e.g., including but not limited to video, heart rate, and temperature). Microcontroller 803 may interface with military and commercial radios or may utilize built in wireless and Bluetooth capability. ANC module 809 may be used for sound compression and/or limiting and blanking out high noise levels as previously described. Handler module 802 may be provided with simple push button or other any other simple interface 807 that is easy to use and manipulate with gloves or in low light. Microcontroller 805 may interface with a range of military and commercial radios 806 or utilize built in Wireless or Bluetooth® capabilities. If using Bluetooth® or wireless means to communicate with the dog, a mobile communication device (e.g., smart phones, tablets) may be configured using a suitable software app to replace the functionalities of microcontroller 805, interface 807 and radio 806. Mobile device 808 may also be used to record, analyze, observe and store sensor 804 data.

An exemplary, hearing protection and communication device for animals such as military working dogs and hunting dogs may include the following components and/or capabilities:

(A) Short-Range Communications Sub-System

A miniature radio receiver 904 with a frequency range of 225-450 MHZ, 1250-1390 MHz, and 1750-1850 MHz may be built into the collar unit of the dog and may communicate with a Rifleman Radio or using Bluetooth® to another suitable communication device. Similarly, frequency range of 30 to 512 MHz may be used to communicate with the Multiband Inter/Intra Team Radio (MBITR). A simplified antenna may be built into the collar unit to enable short distance communication (approximately 50 meters) between the dog and the handler. The Rifleman Radio has 50 preset channels and 5 talk groups per preset, while the MBITR has 100 preset channels and menu selectable talk groups. In the exemplary hearing protection and recording system for dogs, for ease of use, the dog's receiver may be assigned to a single talk group comprising the handler and the dog to prevent the dog from becoming confused by other radio chatter.

(B) User Interface/Controller

A user interface such as the Invisio V50 (made by Invisio Communications, Denmark) may be configured such that a set of push buttons may be preset to select voice or radio communication between the handler to the dog. A handler may assign the dog's talk group to an unused or less used push to talk (PTT) button on the user interface. for communication with the dog. Alternately, a simple single radio connection for the handler may be used with a PTT button to communicate with the dog. The interface is preferably capable of providing the following features: (a) integrate existing and covert operational communications systems to support stand-alone and unit operations; (b) capable of communicating with MWD and handler's group (humans), with communication with MWD assigned to separate PTT group; (c) bypass capability that allows the handler to bypass noise reduction to allow the handler to provide commands to the MWD. Features of bypass include: (1) compressing speech and mixing a radio signal into an active control signal or command. It may be difficult to filter undesired signal because an open microphone reduces communication effectiveness and increases noise levels, (2) adjusting the gain of the playback signal (sensed from an external microphone) to allow the dog to hear ambient sounds at low noise levels, (3) playback of prerecorded commands to prevent playback of environmental noise and (4) compressing/filtering and passing acoustic commands to the MWD at higher frequencies where noise levels are about 20 dB and 40 dB below background noise, and outside human hearing, which is less than about 20 kHz. Use of high frequency commands will not only improve the ability of the MWD to interpret commands in a noisy environment but also provide covert communication capability. Dogs can hear up to about 45 kHz (compared to about 20 kHz for humans). Most ambient noises roll off at about 10 kHz. By transmitting at higher frequencies, background noise is minimized, and the dog should be able to hear sounds that are out of the range of human hearing. Options for direct acoustic or radio communication will enable on-leash or off-leash and single handler or team operations.

(C) Optional Features of System

As previously described, real-time information/data such a dog's heart rate, body temperature and the like provided by sensor 804 measurements may be used to determine the health and wellbeing of the dog. The heart rate and body temperature (for example, inside the ear) of the dog may be measured and correlated to the dog's response to an external event (psychoacoustic responses) in instances where the dog's bark may not be heard by the handler when the dog is off-leash. Optionally, brain mapping sensor, may also be used to monitor hearing performance or measure the cognitive state of the dog. For example, a mapping of brain activity to external triggers may be used to provide a signal that allows a handler to determine whether the dog has detected something of interest, for example, like an explosive. The handler may also detect if the dog is getting tired or overloaded and needs rest.

Communication between the handler and the canine may be encrypted. Acoustic communication may be encrypted such that a message sent from a handler device is transmitted at a frequency of at least 20 kHz and preferably between about 20 kHz and about 40 kHz. Communication may be unencrypted at the ear muff to the dog's normal audible frequency range of about 2 kHz and about 4 kHz. Shifting acoustic communication to higher frequencies may also improve intelligibility (the ability of the dog to better understood the handler's commands) by avoiding frequencies with high environmental noise levels. Similarly, radio communication from the handler to the canine may also be encrypted to prevent unauthorized listeners from intercepting commands and/or sending unauthorized commands. Communication component 800 may comprise a bypass element to enable the handler to electronically bypass passive noise reduction.

In an exemplary hearing protection device, component 200 may be manufactured as a single composite foam piece or cup with varying properties (for example, pore density, pore size, pore length) along the thickness, along its edges, and/or the length of the foam piece instead of using two distinct foam pieces as described previously. The dimensions of component 200 may easily be changed to fit a variety of ear types and head shapes. Component 200 may be formed in the shape of an ear cup formed from a custom mold. A molded foam cup may be made from at least one of a polyurethane foam (e.g., as supplied by Northstar Polymers) and liquid silicone rubbers. An exemplary foam material is FlexFoam-iT supplied by Smooth-On Inc. (Macungie, PA). Exemplary liquid silicone rubbers (LSR) are supplied by U.S. Composites (West Palm Beach, FL), Dow Corning, and Smooth-On Inc. LSR is highly durable and is used for a wide range of commercial, industrial, and medical applications. The density and stiffness of the foam or LSR material may be optimized by varying the ratio between the polymer and additives such as curing agents. The density of the LSR material may be between about 1.05 g/cc and about 1.20 g/cc and preferably between about 1.05 g/cc and about 1.10 g/cc. Denser materials provide improved sound attenuation while lower density materials are more flexible. The composition of the material may be modified to provide the best combination of fit and sound attenuation. In addition, the molded ear cups may more easily be shaped to better conform to the shape of the canine's head, thereby producing a sleeker appearance and ensuring that the sleeve does not slip off, for example, when the canine runs through shrubs, tree branches during bomb sniffing and sentry activities. The dimensions of the mold may be modified to fit a variety of ear sizes and head shapes. Molds may be machined or created using a 3-D printer, either for individual dogs or for generic sizes.

Exemplary noise reduction component 250 (FIGS. 13A-C) may be fabricated in the form of a molded cup using Ecoflex™ liquid silicone rubbers supplied by Smooth-On, Inc. These LSR elastomeric materials are comprised of platinum catalyzed silicone rubbers and are typically supplied in a two-part kit, namely, Part A and Part B. Molded noise reduction component 250 for military working dogs (typically German Shepherds) may comprise an external surface 251 with an arch-shaped end 252 disposed opposite to a horizontal straight end 253. Ends 252 and 253 may be connected using vertical ends 254 and angled ends 255. Internal surface 256 may be in the form of a ring 257 that is disposed along the edges of surface 256. While the width of the ring may be substantially uniform, the thickness of component 250 may vary such the thickness at the arch-shaped end 252 is less than the thickness at straight end 253. Exemplary component 250 is configured to form a good seal between the dog's external ear and ring 257 and also to conform to the shape of the dog's head. In exemplary component 250 designed for a military working dog (e.g., German Shepherds), ring 257 may have a thickness between about 0.4 in. and about 0.6 in. and is preferably about 0.5 in. The thickness of component 250 at straight end 253 may be about 1 in. and the thickness at the arch-shaped end 252 may be about 0.25 in. Arch-shaped end 252 may have a radius of about 2.5 in. Component 250 designed for a military working dog may weigh between about 150 g and about 200 g.

In an exemplary fabrication method for making component 250, about equal amounts of Part A and Part B of Ecoflex™ LSR material are mixed thoroughly at ambient (room) temperatures for between about 2 min. and about 6 min. "Ambient" temperature means temperatures of between about 20° C. and about 25° C. The mixing time is preferably about 3 min. The mixed viscosity of the LSR material is typically between about 2000 cps and about 5000 cps and is preferably about 3000 cps. The mixture may be degassed for between about 2 min. and 5 min. Typically, the degassing time is about 3 min. Degassing may be done using a vacuum chamber that is evacuated at vacuum levels of between about 10 mm Hg and about 50 mm Hg. Preferably, the vacuum level used is about 30 mm Hg. The LSR material is then fed to a mold of desired predetermined shape while ensuring that no residual air bubbles or air pockets are present in the mold after filling the mold with the LSR material. The shape of the mold may depend on the shape and size of the dog's head and ears. The mixed LSR may be pumped or injected into a suitable mold made of 6061 Aluminum Alloy. The material may then be allowed to cure for about 4 h at ambient temperature. The material may then be cured at elevated temperatures; for example, at about 80° C. for about 2 h and at 100° C. for about 1 h.

Example

Effectiveness of Exemplary Hearing Protection Devices Using Various Noise Reduction Components The noise reduction potential of an exemplary hearing protection device comprising exemplary passive noise reduction composite component 200 was compared to that measured using an exemplary molded noise reduction component 250. Component 200 comprised an MLV backing whereas component 250 did not comprise an MLV backing. Component 250 was made using Ecoflex™ 00-30 LSR material. Input noise with frequencies of up to 10 kHz was used during this evaluation. At frequencies above about 2500 Hz, component 200 resulted in better attenuation of up to about 48 dB (FIG. 14). However, at the frequencies below 2 kHz, as commonly found in battlefield scenarios, the molded noise reduction component 250 provided superior noise reduction capabilities, in particular, at frequencies between about 1000 Hz and 2000 Hz. The exemplary device using exemplary molded noise reduction components may be characterized by a noise reduction of between about 20 dB and about 30 dB at noise frequencies of between about 1000 Hz and about 2000 Hz.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

What is claimed is:

1. A flexible hearing protection device for a dog comprising:
   a sleeve made of stretchable fabric including:
      an inside surface;
      a reinforcing wear strip disposed along a length of the sleeve and joined to a first region associated with an outside surface opposing the inside surface; and
      a pair of donning/doffing tabs, each attached to a respective end of the reinforcing wear strip and configured to be out of the line of the sight of the dog when the sleeve is installed on the dog's head, wherein the sleeve is configured to be slipped on to the dog's head by pulling the sleeve over the dog's jaws using the pair of donning/doffing tabs;
   a pair of flexible passive noise reduction components, each insertable into a respective housing cover joined to the inside surface of the sleeve, each noise reduction component configured to form a seal with the surface of an external ear of the dog when the sleeve is installed on the dog's head; and
   a drawstring disposed opposite the reinforcing strip and configured to removably tighten the sleeve to the dog's neck to conform each flexible passive noise reduction component to each ear and create the seal between each of the noise reduction components and the surface of each of the dog's external ears, wherein the hearing protection device is conformable to the shape of the dog's head and external ears and minimizes peak pressure points on the dog's head.

2. The hearing protection device of claim 1, wherein the sleeve is made of a material including between about 60% to about 70% nylon and between about 30% and about 40% spandex.

3. The hearing protection device of claim 1, wherein the drawstring is inserted through a plurality of grommets disposed in the sleeve and adjustably tightened to the dog's neck using a stop-cord lock.

4. The hearing protection device of claim 1, wherein each passive noise reduction component comprises a composite structure made of polymeric closed cell foam materials.

5. The hearing protection device of claim 4, wherein each passive noise reduction component comprises a first polymeric closed cell foam material comprising a mass loaded vinyl (MLV) material backing on one side and a second closed cell foam material ring disposed along the edges of the first foam material on the side opposite to the side including the mass loaded vinyl (MLV) backing, wherein the second closed cell foam material ring is configured to form a seal with the dog's external ear when the sleeve is installed.

6. The hearing protection device of claim 5, wherein the second closed cell foam material comprises ethylene propylene diene monomer (EPDM).

7. The hearing protection device of claim 5, wherein the mass loaded vinyl (MLV) material comprises barium infused mass loaded polyvinyl chloride.

8. The hearing protection device of claim 1, further comprising passive noise reduction electronic bypass components configured for each ear, wherein the amplitude of sound playback into each ear is adjusted depending upon external sound levels and at external sound frequencies between about 100 Hz and about 15 kHz.

9. The hearing protection device of claim 8, wherein the electronic bypass components comprise an internal microphone for each ear, an external microphone for each ear, a speaker for each ear, and a control module.

10. The hearing protection device of claim 9, wherein the internal microphone and speaker associated with each ear are substantially housed within the passive noise reduction component corresponding to each respective ear.

11. The hearing protection device of claim 1, wherein each passive noise reduction component comprises a molded cup made of at least one of a polyurethane foam material and liquid silicone rubber (LSR) material wherein the cup is shaped to conform to the shape of dog's head and external ear.

12. The hearing protection device of claim 11, wherein the density of the LSR material of the ear cup is between about 1.05 g/cc and about 1.20 g/cc.

13. A flexible hearing protection device for a dog comprising:
a sleeve made of stretchable fabric including;
an inside surface;
a reinforcing wear strip disposed along a length of the sleeve and joined to a first region associated with an outside surface opposing the inside surface; and
a pair of donning/doffing tabs, each attached to a respective end of the reinforcing wear strip and configured to be out of the line of the sight of the dog when the sleeve is installed on the dog's head, wherein the sleeve is configured to be slipped on to the dog's head by pulling the sleeve over the dog's jaws using the pair of donning/doffing tabs;
a pair of flexible passive noise reduction components, each insertable into a respective housing cover joined to the inside surface of the sleeve, each noise reduction component configured to form a seal with the surface of an external ear of the dog when the sleeve is installed on the dog's head;
a drawstring disposed opposite the reinforcing strip and configured to removably tighten the sleeve to the dog's neck to conform each flexible passive noise reduction component to each ear and create the seal between each of the noise reduction components and the surface of each of the dog's external ears;
at least one of passive noise reduction electronic bypass components and active noise cancellation (ANC) components for adjusting the level of noise reduction in each of the dog's ear; and a communication component configured to enable the dog's handler to communicate with the dog, wherein the hearing protection device is conformable to the shape of the dog's head and external ears and minimizes peak pressure points on the dog's head.

14. The hearing protection device of claim 13, wherein the passive noise reduction electronic bypass components comprise an internal microphone, an external microphone for each ear, a speaker for each ear, and a control module.

15. The hearing protection device of claim 13, wherein the ANC components comprise an internal microphone for each ear, an external microphone for each ear, a speaker for each ear, and a control module capable of attenuating external noise at frequencies below about 1000 Hz in each of the dog's ear.

16. The hearing protection device of claim 13, wherein each passive noise reduction component comprises a molded cup made of at least one of a polyurethane foam material and liquid silicone rubber (LSR) material, wherein the cup is shaped to conform to the shape of the dog's head and external ear.

17. The hearing protection device of claim 16, wherein the density of the LSR material of the ear cup is between about 1.05 g/cc and about 1.20 g/cc.

18. A flexible hearing protection device for a dog comprising:
a sleeve made of stretchable fabric including;
an inside surface;
a reinforcing wear strip disposed along a length of the sleeve and joined to a first region associated with an outside surface opposing the inside surface; and
a pair of donning/doffing tabs, each attached to a respective end of the reinforcing wear strip and configured to be out of the line of the sight of the dog when the sleeve is installed on the dog's head, wherein the sleeve is configured to be slipped on to the dog's head by pulling the sleeve over the dog's jaws using the pair of donning/doffing tabs;
a pair of flexible molded passive noise reduction components made of liquid silicone rubber, each insertable into a respective housing cover joined to the inside surface of the sleeve, each noise reduction component configured to form a seal with the surface of an external ear of the dog when the sleeve is installed on the dog's head; and
a drawstring disposed opposite the reinforcing strip and configured to removably tighten the sleeve to the dog's neck to conform each flexible passive noise reduction component to each ear and create the seal between each of the noise reduction components and the surface of each of the dog's external ears, wherein the hearing protection device is conformable to the shape of the dog's head and external ears and minimizes peak pressure points on the dog's head.

19. The hearing protection device of claim 18, wherein the liquid silicone rubber prior to curing has a mixed viscosity of about 3000 cps.

20. The hearing protection device of claim 18, wherein the device is characterized by a noise reduction of between about 20 dB and about 30 dB at noise frequencies of between about 1000 Hz and about 2000 Hz.

21. The hearing protection device of claim 18, wherein each molded noise reduction component comprises:
an internal surface comprising a cup-shaped structure bounded by a ring wherein the ring is configured to seal with each external ear surface of the dog; and,
a planar external surface disposed opposite to the internal surface wherein each of the internal and external surface comprises an arch-shaped end disposed opposite to a straight end.

22. The hearing protection device of claim 21, wherein a thickness of the molded noise reduction component at the straight end is greater than a thickness at the arch-shaped end.

23. A method for fabricating the molded noise reduction component of claim 18, the method comprising:
selecting a liquid silicone rubber material (LSR) characterized by a mixed viscosity of about 3000 cps prior to curing;
degassing the mixed LSR material by exposing the material to a vacuum;
feeding the degassed LSR material into a mold of predetermined shape; and
curing the degassed LSR material.

24. The method of claim 23, wherein the mold is made of Aluminum 6061 Alloy.

* * * * *